US012387508B2

(12) United States Patent
Liu et al.

(10) Patent No.: US 12,387,508 B2
(45) Date of Patent: Aug. 12, 2025

(54) DIRECT CLASSIFICATION OF RAW BIOMOLECULE MEASUREMENT DATA

(71) Applicant: PrognomIQ, Inc., San Mateo, CA (US)

(72) Inventors: Manway Liu, Burlingame, CA (US); Chinmay Belthangady, San Jose, CA (US); Bruce Wilcox, Keezletown, VA (US); Philip Ma, San Jose, CA (US); Joon-Yong Lee, Richland, WA (US); Hyungseok Kim, Cambridge, MA (US)

(73) Assignee: PrognomIQ, Inc., San Mateo, CA (US)

( * ) Notice: Subject to any disclaimer, the term of this patent is extended or adjusted under 35 U.S.C. 154(b) by 484 days.

(21) Appl. No.: 17/930,663

(22) Filed: Sep. 8, 2022

(65) Prior Publication Data

US 2023/0080329 A1 Mar. 16, 2023

Related U.S. Application Data

(60) Provisional application No. 63/242,890, filed on Sep. 10, 2021.

(51) Int. Cl.

| | |
|---|---|
| *G06V 20/69* | (2022.01) |
| *G06N 3/0464* | (2023.01) |
| *G06V 10/77* | (2022.01) |
| *G06V 10/774* | (2022.01) |
| *G16B 15/00* | (2019.01) |
| *G16B 20/00* | (2019.01) |

(Continued)

(52) U.S. Cl.
CPC ......... *G06V 20/698* (2022.01); *G06N 3/0464* (2023.01); *G06V 10/7715* (2022.01); *G06V 10/7747* (2022.01); *G06V 20/695* (2022.01); *G16B 15/00* (2019.02); *G16B 20/00* (2019.02); *G16B 40/10* (2019.02); *G16B 40/20* (2019.02)

(58) Field of Classification Search
CPC ............... G06V 20/698; G06V 20/695; G06V 10/7747; G06V 10/7715; G16B 15/00; G16B 40/10; G16B 20/00; G16B 40/20; G06N 3/0464
See application file for complete search history.

(56) References Cited

U.S. PATENT DOCUMENTS

| | | | |
|---|---|---|---|
| 7,632,686 B2 | 12/2009 | Anderson | |
| 7,749,299 B2 | 7/2010 | Vanheusden et al. | |

(Continued)

FOREIGN PATENT DOCUMENTS

| | | |
|---|---|---|
| CA | 2787201 A1 | 7/2011 |
| CA | 3126990 A1 | 8/2020 |

(Continued)

OTHER PUBLICATIONS

Kantz, Edward D., et al. "Deep neural networks for classification of LC-MS spectral peaks." Analytical chemistry 91.19 (2019): 12407-12413. (Year: 2019).*

(Continued)

*Primary Examiner* — Utpal D Shah
(74) *Attorney, Agent, or Firm* — Wilson Sonsini Goodrich & Rosati

(57) ABSTRACT

Disclosed herein are systems and methods for direct classification of biological datasets. The datasets may include raw mass spectrometry data. Some aspects include training a classifier for direct classification of raw data, and some aspects include applying the classifier.

20 Claims, 11 Drawing Sheets

(51) Int. Cl.
  *G16B 40/10* (2019.01)
  *G16B 40/20* (2019.01)

(56) References Cited

U.S. PATENT DOCUMENTS

| | | | |
|---|---|---|---|
| 7,906,758 B2 | 3/2011 | Stults et al. | |
| 9,002,652 B1 | 4/2015 | Hood et al. | |
| 9,005,994 B2 | 4/2015 | Huo | |
| 9,234,895 B2 | 1/2016 | Hood et al. | |
| 9,394,332 B2 | 7/2016 | Markert-Hahn et al. | |
| 9,445,994 B2 | 9/2016 | Irvine et al. | |
| 9,549,901 B2 | 1/2017 | Shi et al. | |
| 9,589,374 B1 | 3/2017 | Gao et al. | |
| 9,868,756 B2 | 1/2018 | Markert-Hahn et al. | |
| 9,984,201 B2 | 5/2018 | Zhang et al. | |
| 10,288,588 B2 * | 5/2019 | Morris | G01N 33/2829 |
| 10,466,230 B2 | 11/2019 | Stults et al. | |
| 10,829,816 B2 | 11/2020 | Staker et al. | |
| 10,866,242 B2 | 12/2020 | Farokhzad et al. | |
| 11,085,931 B2 | 8/2021 | Warthoe | |
| 12,007,397 B2 | 6/2024 | Wilcox et al. | |
| 12,087,405 B2 | 9/2024 | Blume et al. | |
| 2004/0213446 A1 * | 10/2004 | Shams | G06T 5/50 382/129 |
| 2005/0048489 A1 | 3/2005 | Thompson et al. | |
| 2005/0221314 A1 | 10/2005 | Berlin et al. | |
| 2006/0008618 A1 | 1/2006 | Wang et al. | |
| 2007/0259363 A1 | 11/2007 | Amri et al. | |
| 2008/0187207 A1 | 8/2008 | Bhanot et al. | |
| 2008/0291122 A1 | 11/2008 | Smith et al. | |
| 2009/0090855 A1 | 4/2009 | Kobold et al. | |
| 2009/0176228 A1 | 7/2009 | Birse et al. | |
| 2010/0042329 A1 | 2/2010 | Hood et al. | |
| 2010/0188075 A1 | 7/2010 | Litvinov et al. | |
| 2011/0117582 A1 | 5/2011 | Malima et al. | |
| 2011/0171323 A1 | 7/2011 | Weiss | |
| 2011/0215237 A1 | 9/2011 | Bateman | |
| 2012/0046184 A1 | 2/2012 | Dawson et al. | |
| 2012/0208282 A1 * | 8/2012 | Deigner | G16B 40/10 324/309 |
| 2013/0080073 A1 * | 3/2013 | de Corral | G01N 30/86 702/23 |
| 2013/0217057 A1 | 8/2013 | Kearney et al. | |
| 2014/0063009 A1 | 3/2014 | Buehler et al. | |
| 2014/0106976 A1 | 4/2014 | Sachs et al. | |
| 2015/0105276 A1 | 4/2015 | Hofmann et al. | |
| 2015/0253341 A1 | 9/2015 | McAvoy et al. | |
| 2016/0032395 A1 | 2/2016 | Davicioni et al. | |
| 2016/0047820 A1 | 2/2016 | Kearney et al. | |
| 2016/0054300 A1 | 2/2016 | Winther et al. | |
| 2016/0154006 A1 | 6/2016 | Hermanson et al. | |
| 2016/0260594 A1 | 9/2016 | Hendricks | |
| 2017/0024641 A1 | 1/2017 | Wierzynski | |
| 2017/0051073 A1 | 2/2017 | Hynes et al. | |
| 2017/0076195 A1 | 3/2017 | Yang et al. | |
| 2017/0220734 A1 | 8/2017 | Colavin et al. | |
| 2017/0277844 A1 | 9/2017 | Apte et al. | |
| 2018/0067119 A1 | 3/2018 | Kearney et al. | |
| 2018/0068083 A1 | 3/2018 | Cohen et al. | |
| 2018/0086713 A1 | 3/2018 | Elkon et al. | |
| 2018/0172694 A1 | 6/2018 | Farokhzad et al. | |
| 2018/0274039 A1 | 9/2018 | Zhang et al. | |
| 2018/0275143 A1 | 9/2018 | Wilcox et al. | |
| 2019/0018019 A1 * | 1/2019 | Shan | G16B 40/10 |
| 2019/0147983 A1 | 5/2019 | Shan et al. | |
| 2019/0256924 A1 | 8/2019 | Vogelstein et al. | |
| 2019/0328837 A1 | 10/2019 | Kim et al. | |
| 2020/0002375 A1 | 1/2020 | Chowdhury | |
| 2020/0025765 A1 | 1/2020 | Agorreta Arrazubi et al. | |
| 2020/0025766 A1 | 1/2020 | Hanash et al. | |
| 2020/0381083 A1 | 12/2020 | Chen | |
| 2021/0000965 A1 | 1/2021 | Wang et al. | |
| 2021/0005327 A1 | 1/2021 | Anwar et al. | |
| 2021/0017598 A1 | 1/2021 | Jain et al. | |
| 2021/0031166 A1 | 2/2021 | Porter et al. | |
| 2021/0072255 A1 | 3/2021 | Farokhzad et al. | |
| 2021/0098083 A1 | 4/2021 | Ma et al. | |
| 2021/0104321 A1 | 4/2021 | Lipsky et al. | |
| 2021/0132071 A1 | 5/2021 | Kostarelos et al. | |
| 2021/0174958 A1 | 6/2021 | Drake et al. | |
| 2021/0302416 A1 | 9/2021 | Soldo et al. | |
| 2021/0375604 A1 | 12/2021 | Gajadhar et al. | |
| 2022/0148680 A1 | 5/2022 | Blume et al. | |
| 2022/0237930 A1 * | 7/2022 | Rando | G06V 10/764 |
| 2022/0259202 A1 | 8/2022 | Meimetis | |
| 2022/0260559 A1 | 8/2022 | Blume et al. | |
| 2022/0299527 A1 | 9/2022 | Bateman et al. | |
| 2022/0317014 A1 | 10/2022 | Peterman et al. | |
| 2022/0328129 A1 | 10/2022 | Ma et al. | |
| 2022/0328134 A1 * | 10/2022 | Ma | G16B 20/00 |
| 2022/0334118 A1 | 10/2022 | Blume et al. | |
| 2023/0145645 A1 | 5/2023 | Wilcox et al. | |
| 2023/0178176 A1 | 6/2023 | Manway et al. | |
| 2023/0266328 A1 | 8/2023 | Hadjidemetriou et al. | |
| 2024/0280558 A1 * | 8/2024 | Platt | G01N 33/48792 |
| 2024/0395362 A1 | 11/2024 | Blume et al. | |
| 2025/0093363 A1 | 3/2025 | Wilcox et al. | |

FOREIGN PATENT DOCUMENTS

| | | |
|---|---|---|
| CN | 102985819 A | 3/2013 |
| CN | 109416926 A | 3/2019 |
| CN | 109470859 A | 3/2019 |
| EP | 1342794 B1 | 12/2005 |
| EP | 1394173 B1 | 10/2007 |
| EP | 2124051 A1 | 11/2009 |
| EP | 2524219 A2 | 11/2012 |
| EP | 2921858 A1 | 9/2015 |
| EP | 3510402 A1 | 7/2019 |
| EP | 3554681 A1 | 10/2019 |
| EP | 4096694 A1 | 12/2022 |
| GB | 2603051 A | 7/2022 |
| JP | 2010539486 A | 12/2010 |
| JP | 2011527414 A | 10/2011 |
| WO | WO-0063683 A1 | 10/2000 |
| WO | WO-2005019477 A2 | 3/2005 |
| WO | WO-2005036180 A1 | 4/2005 |
| WO | WO-2008114917 A1 | 9/2008 |
| WO | WO-2010097785 A1 | 9/2010 |
| WO | WO-2013025759 A1 | 2/2013 |
| WO | WO-2013152989 A2 | 10/2013 |
| WO | WO-2014078855 A1 | 5/2014 |
| WO | WO-2015116837 A1 | 8/2015 |
| WO | WO-2015159293 A2 | 10/2015 |
| WO | WO-2016008451 A1 | 1/2016 |
| WO | WO-2016207391 A1 | 12/2016 |
| WO | WO-2017106481 A1 | 6/2017 |
| WO | WO-2017192965 A2 | 11/2017 |
| WO | WO-2017212428 A1 | 12/2017 |
| WO | WO-2018046542 A1 | 3/2018 |
| WO | WO-2018112460 A1 | 6/2018 |
| WO | WO-2018119216 A1 | 6/2018 |
| WO | WO-2018161031 A1 | 9/2018 |
| WO | WO-2018170518 A1 | 9/2018 |
| WO | WO-2019050966 A2 | 3/2019 |
| WO | WO-2019067092 A1 | 4/2019 |
| WO | WO-2019182885 A1 | 9/2019 |
| WO | WO-2019200410 A1 | 10/2019 |
| WO | WO-2019209888 A1 | 10/2019 |
| WO | WO-2020096631 A2 | 5/2020 |
| WO | WO-2020198209 A1 | 10/2020 |
| WO | WO-2021026172 A1 | 2/2021 |
| WO | WO-2021087407 A1 | 5/2021 |
| WO | WO-2021154893 A1 | 8/2021 |
| WO | WO-2022020272 A1 | 1/2022 |
| WO | WO-2022072471 A1 | 4/2022 |
| WO | WO-2022182989 A1 | 9/2022 |
| WO | WO-2022212583 A1 | 10/2022 |
| WO | WO-2023019148 A1 | 2/2023 |
| WO | WO-2023039479 | 3/2023 |
| WO | WO-2023039579 | 3/2023 |
| WO | WO-2023164697 | 8/2023 |
| WO | WO-2023240046 A2 | 12/2023 |
| WO | WO-2024054946 A1 | 3/2024 |

(56) References Cited

FOREIGN PATENT DOCUMENTS

OTHER PUBLICATIONS

Paschke, C., et al. "Mirion—a software package for automatic processing of mass spectrometric images." Journal of the American Society for Mass Spectrometry 24.8 (2013): 1296-1306. (Year: 2013).*

Melnikov, Arsenty D., Yuri P. Tsentalovich, and Vadim V. Yanshole. "Deep learning for the precise peak detection in high-resolution LC-MS data." Analytical chemistry 92.1 (2019): 588-592. (Year: 2019).*

Palagi, Patricia M., et al. "MSight: An image analysis software for liquid chromatography-mass spectrometry." Proteomics 5.9 (2005): 2381-2384. (Year: 2005).*

Agajanian, et al., Integration of Random forest classifiers and deep convolutional neural networks for classification and Biomolecular modeling of cancer driver mutations. Frontiers in molecular biosciences 6 (2019): 44. Jun. 11, 2019, Retrieved on Oct. 30, 2022. From https://www.frontiersin.org/articles/10.3389/fmolb.2019.00044/full entire document.

Brinkmann et al., Oral squamous cell carcinoma detection by salivary biomarkers in a Serbian population, Oral Oncology, vol. 47(1), 2011: pp. 51-55.

Co-pending U.S. Appl. No. 18/164,446, inventors Ma; Philip et al., filed Feb. 3, 2023.

Correia, et al., Machine learning modeling of blood lipid biomarkers in familial hypercholesterolaemia versus polygenic/environmental dyslipidemia. Nature portfolio, Scientific Reports (2021) 11:3801; 9 Pages.

Cruz et al., Applications of Machine learning in cancer prediction and prognosis (Cancer Informatics, 2006, vol. 2, pp. 59-77).

"Seer, Inc. Form 10-Q For Quarterly period ended Jun. 30, 2021." Edgar. Securities and Exchange Commission, 2021, https://www.sec.gov/ix?doc=/Archives/edgar/data/0001726445/000162828021016865/seer-20210630.htm.

GB2205374.8 Examination Report dated Apr. 19, 2023.

Hsu, T. et al., Plasma-based detection of pancreatic cancer: A multiomics approach. Poster presented at the 2021 AACR virtual special conference: Pancreatic cancer, Sep. 29-30, 2021; 10 Pages.

Katzke, et al., Blood lipids and lipoproteins in relation to incidence and mortality risks for CVD and cancer in the prospective EPIC-Heidelberg cohort, BMC Medicine (2017) 15:218; 13 Pages.

Kopac. Protein corona, understanding the nanoparticle-protein interactions and future perspectives. International Journal of Biological Macromolecules 2021, vol. 169, pp. 290-301, published online Dec. 21, 2020 (Year: 2020).

Kuang, M. et al., Proteomic analysis of plasma exosomes to differentiate malignant from benign pulmonary nodules. Clin Proteom 16, 5 (2019). https://doi.org/10.1186/s12014-019-9225-5.

Lennon, A. M. et al., Feasibility of blood testing combined with PET-CT to screen for cancer and guide intervention. Science 369, eabb9601 (2020). DOI: 10.1126/science. abb9601.

Li, Xiao-jun et al., A Blood-Based Proteomic Classifier for the Molecular Characterization of Pulmonary Nodules. Sci Transl Med. Oct. 16, 2013; 5(207): 207ra142. doi:10.1126/scitranslmed. 3007013.

Lin, C. J. et al., Evaluation of a sensitive blood test for the detection of colorectal advanced adenomas in a prospective cohort using a multiomics approach. Poster Presented at the 2021 Gastrointestinal Cancers Symposium. 1 Page.

Liu, et al., Machine Learning Protocols in Early Cancer Detection Based on Liquid Biopsy: A Survey. Life 2021, 11, 638,39 Pages. https://doi.org/ 10.3390/life11070638.

Melone. Seer debuts with proprietary proteomics platform to enable early detection of cancer and neurological diseases. Businesswire 2018, pp. 1-5 (Year: 2018).

Mishra et al. Biological effects of formation of protein corona onto nanoparticles. International Journal of Biological Macromolecules 2021, vol. 175, pp. 1-18, published on line Jan. 21, 2021 (Year: 2021).

Nguyen, et al., Protein corona: a new approach for nanomedicine design, International Journal of Nanomedicine 2017:12; 3137-3151.

PCT/US2022/076125 International Search Report and Written Opinion dated Jan. 12, 2023.

PCT/US2023/063358 International Search Report and Written Opinion dated Aug. 1, 2023.

Pearson, Ryan M., Vanessa V. Juettner, and Seungpyo Hong. "Biomolecular corona on nanoparticles: a survey of recent literature and its implications in targeted drug delivery." Frontiers in chemistry 2 (2014): 108.

Putcha, G. et al., Blood-based detection of early-stage colorectal cancer using multiomics and machine learning. Poster presented at American Society of Clinical Oncology. 2020, 1 Page.

Ritz, et al.,, Protein Corona of Nanoparticles: Distinct Proteins Regulate the Cellular Uptake, Biomacromolecules 2015:16(4); 1311-1321 DOI: 10.1021/acs.biomac.5b00108.

Shriwash et al., Identification of differentially expressed genes in small and non-small cell lung cancer based on meta-analysis of mRNA, 2019, Heliyon, 5, p. 1-9 (Year: 2019).

Tanigawa et al. Upregulation of ANGPTL6 in mouse keratinocytes enhances susceptibility to psoriasis. Sci Rep. Oct. 4, 2016;6:34690. doi: 10.1038/srep34690. PMID.

Trivedi et al. Risk assessment for indeterminate pulmonary nodules using a novel, plasma-protein based biomarker assay. Biomed Res Clin Pract 2018, 3(4), pp. 1-17 (Year: 2018).

U.S. Appl. No. 17/585,303 Notice of Allowance dated Apr. 26, 2023.

U.S. Appl. No. 17/585,303 Office Action dated Mar. 6, 2023.
U.S. Appl. No. 17/709,185 Office Action dated Jun. 15, 2023.
U.S. Serial No. 17/709, 185 Office Action dated Mar. 16, 2023.
U.S. Appl. No. 17/709,202 Office Action dated Jan. 26, 2023.
U.S. Appl. No. 17/709,202 Office Action dated May 10, 2023.
U.S. Serial No. 17/720, 197 Office Action dated Aug. 11, 2023.
U.S. Appl. No. 17/931,469 Office Action dated Apr. 3, 2023.
U.S. Appl. No. 17/931,469 Office Action dated May 25, 2023.
U.S. Appl. No. 17/931,469 Office Action dated Sep. 19, 2023.
U.S. Appl. No. 18/095,422 Office Action dated Apr. 14, 2023.
U.S. Appl. No. 18/095,422 Office Action dated Jun. 13, 2023.
U.S. Appl. No. 18/150,390 Office Action dated Jul. 5, 2023.
U.S. Appl. No. 18/164,446 Office Action dated Jul. 19, 2023.
U.S. Appl. No. 18/165,264 Office Action dated Aug. 11, 2023.
U.S. Appl. No. 17/585,303 Notice of Allowance dated Apr. 14, 2023.

Walkey et al. ("Protein Corona Fingerprinting Predicts the Cellular Interaction of Gold and Silver Nanoparticles," ACS Nano, vol. 8, No. 3, pp. 2439-2455, published 2014) (Year: 2014).

Wan et al. ("Highly Specific Electrochemical Analysis of Cancer Cells using Multi-Nanoparticle Labeling," Angew. Chem. Int. Ed. 2014, vol. 53, pp. 13145-13149) (Year: 2014).

Zeng et al., Integrative Models of Histopathological Image Features and Omics Data Predict Survival in Head and Neck Squamous Cell Carcinoma, Frontiers in Cell and Development Biology, 2020; vol. 8: p. 55309, Available online at: https://www.frontiersin.org/articles/10.3389/fcell.2020.553099/full [accessed Apr. 14, 2023].

Zhang et al., Phenotype Classification using Proteome Data in a Data-Independent Acquisition Tensor Format. J Am Soc Mass Spectrom. Nov. 4, 2020;31(11):2296-2304. doi: 10.1021/jasms.0c00254. Epub Oct. 26, 2020. PMID: 33104352.

Acharjee et al. Integration of metabolomics, lipidomics and clinical data using a machine learning method. BMC Bioinformatics. 2016; 17(Suppl 15): 37-49.

"Adalsteinsson, V.A., Ha, G., Freeman, S.S. et al. Scalable whole-exome sequencing of cell-free DNA reveals high concordance with metastatic tumors. Nat Commun 8, 1324 (2017). https://doi.org/10.1038/s41467-017-00965-y".

Albers, et al., Dating genomic variants and shared ancestry in population-scale sequencing data. PLOS Biology, Jan. 2020, 18(1): 19 Pages. https://doi.org/10.1371/journal.pbio.3000586.

Alcalá et al. The Anthrax Toxin receptor 1 (ANTXR1) Is enriched in pancreatic cancer stem cells derived from primary tumor cultures. Stem Cells International, 2019, Article ID:1378639, 1-13 pages.

Altobelli et al. HtrA1: Its future potential as a novel biomarker for cancer. Oncology Reports, 2015, 34:555-566.

(56) References Cited

OTHER PUBLICATIONS

Andreeva, A.V., and Kutuzov, M.A. Cadherin 13 in cancer. Genes Chromosomes Cancer, 2010, 49(9):775-90.

Armagan, et al., Generalized Beta Mixtures of Gaussians. Advances in neutral information processing systems. Mar. 13, 2012; 1-9 Pages.

Arroyo et al. Expression-based, consistent biomarkers for prognosis and diagnosis in lung cancerClin Transl Oncol, 2020; 22(10):1867-1874.

Bakry et al. Protein profiling for cancer biomarker discovery using matrix-assisted laser desorption/ionization time-of-flight mass spectrometry and infrared imaging: A review. Analytica Chimica Acta 2011, vol. 690, pp. 26-34 (Year: 2011).

Bell et al. A HUPO test sample study reveals common problems in mass spectrometry-based proteomics. Nat Methods. Jun. 2009; 6(6): 423-430.

Benjamini e al. Controlling the false discovery rate: a practical and powerful approach to multiple testing. Journal of the Royal Statistical Society. Series B (Methodological). pp. 289-300 (1995).

Bludau, I., Aebersold, R. Proteomic and interactomic insights into the molecular basis of cell functional diversity. Nat Rev Mol Cell Biol 2020;21: 327-340. https://doi.org/10.1038/s41580-020-0231-2.

Blume, et al., Rapid, deep and precise profiling of the plasma proteome with multi-nanoparticle protein corona. Nature Communications, 2020; 11(3662): 1-14.

Bresnick et al. S100 proteins in cancer. Nature Reviews Cancer, 2015, 15:96-109.

Bronsema, K. J. et al; "Internal standards in the quantitative determination of protein biopharmaceuticals using liquidchromatography coupled to mass spectrometry", Journal of Chromatography B, vols. 893-894, 2012, pp. 1-14. (Year: 2012).

"Butler et al., Lipids and Cancer: Emerging roles in pathogenesis, diagnosis and therapeutic intervention. Advanced Drug Delivery Review. 2020; 159:245-293".

Capriotti et al.: Analytical methods for characterizing the nanoparticle-protein corona. Chromatographia 77(11-12):755-769 DOI:10.1007/s10337-014-2677-x (2014).

Caracciolo, et al., Disease-specific protein corona sensor arrays may have disease detection capacity, 2019, Nanoscale Horiz., 4, p. 1063-1076. (Year:2019).

Carbone et al. Angiopoietin-Like proteins in Angiogenesis, Inflammation and cancer. Int J Mol Sci. Feb. 2018; 19(2): 431 (1-22).

"Chantada-Vazquez, et al., Identification of a Profile of Neutrophil-Derived Granule Proteins in the Surface of Gold Nanoparticles after Their Interaction with Human Breast Cancer Sera. Nanomaterials (Basel, Switzerland), 2020; 10(1223): 1-18. https://doi.org/10.3390/nano10061223".

Chantada-Vazquez, et al., Proteomic analysis of the bio-corona formed on the surface of (Au, Ag, Pt)-nanoparticles in human serum. Colloids Surf B Biointerfaces. May 1, 2019;177:141-148. doi: 10.1016/j.colsurfb.2019.01.056. Epub Jan. 29, 2019. PMID: 30721790.

Chantada-Vazquez et al., Proteomic investigation on bio-corona of Au, Ag and Fe nanoparticles for the discovery of triple negative breast cancer serum protein biomarkers. J Proteomics. Feb. 10, 2020;212:103581; 1-19 Pages. doi: 10.1016/j.jprot.2019.103581. Epub Nov. 12, 2019. PMID: 31731051.

Chen, et al., Glycoproteomics analysis of human liver tissue by combination of multiple enzyme digestion and hydrazide chemistry. J Proteome Res. Feb. 2009;8(2):651-61. doi: 10.1021/pr8008012.

Chen et al. Network analysis of differentially expressed smoking-associated mRNAs, lncRNAs and miRNAs reveals key regulators in smoking-associated lung cancer. Exp. Ther. Med., 2018;16: 4991-5002.

Chen, T., Kornblith, S., Norouzi, M. et al. A Simple Framework for Contrastive Learning of Visual Representations. Proceedings of the 37 th International Conference on Machine Learning, Vienna, Austria, PMLR 119, 2020; 11 Pages.

Cho et al. Serum amyloid A is elevated in the serum of lung cancer patients with poor prognosis. Br J Cancer. 2010, 102(12): 1731-1735.

"Choi, et al., DUX4 recruits p300/CBP through its C-terminus and induces global H3K27 acetylation changes. Nucleic Acids Research, 2016. vol. 44m No. 11, 5161-5173.".

"Schwenk, et al., The Human plasma proteome draft of 2017: Building on the human plasma peptideatlas from mass spectrometry and complementary assays. Journal Proteome Research, Dec. 2017; 16(12): 4299-4310.".

Cohen, et al., Combined circulating tumor DNA and protein biomarker-based liquid biopsy for the earlier detection of pancreatic cancers. PNAS, Sep. 5, 2017; 114 (38) 10202-10207, https://doi.org/10.1073/pnas.1704961114.

Cohen, et al., Detection and localization of surgically resectable cancers with a multi-analyte blood test. Science Feb. 23, 2018: vol. 359, Issue 6378, pp. 926-930. DOI: 10.1126/science.aar3247.

Co-pending U.S. Appl. No. 17/931,469, inventors Wilcox; Bruce et al., filed Sep. 12, 2022.

Co-pending U.S. Appl. No. 18/150,390, inventors Ma; Philip et al., filed Jan. 5, 2023.

Corbo, et al., Analysis of the Human Plasma Proteome Using Multi-Nanoparticle Protein Corona for Detection of Alzheimer's Disease. Adv. Healthcare Mater. 2021, 10, 2000948; 1-10 Pages. https://doi.org/10.1002/adhm.202000948.

"Corley, et al., Adenoma Detection Rate and Risk of Colorectal Cancer and Death. New Engl J Med Apr. 2014; 370:1298-1306.".

Cox et al. MaxQuant enables high peptide identification rates, individualized p.p.b.-range mass accuracies and proteome-wide protein quantification. Nat Biotechnol 26:1367-1372 (2008).

Datta, S. et al., Statistical Analysis of Proteomics, Metabolomics, and Lipidomics Data Using Mass Spectrometry. Springer Cham, 2017; 295 Pages.

Demichev et al.: DIA-NN: neural networks and interference correction enable deep proteome coverage in high throughput. Nature Methods 17(1):41-44 DOI:10.1038/s41592-019-0638 (2020).

Domenico, et al., Nanoparticle-biomolecular corona: A new approach for the early detection of non-small-cell lung cancer, 2019, J Cell Physiol., 234, p. 9378-9386. (Year:2019).

Dougan et al. Proteomics-Metabolomics Combined Approach Identifies Peroxidasin as a Protector against Metabolic and Oxidative Stress in Prostate Cancer. Int. J. Mol. Sci., 2019, 20(12):3046.

Epelbaum et al. Haptoglobin-related protein as a Serum marker in Malignant Lymphoma. Pathology Oncology Research, 1998, 4(4):271-276.

Falahati et al., A health concern regarding the protein corona, aggregation and disaggregation, 2019, BBA-General Subjects, 1863, p. 971-991 (Year:2019).

Fan et al. Intelligence Algorithms for Protein Classification by Mass Spectrometry. BioMed Research International, vol. 2018, Article ID 2862458, 11 pages, 2018.

"Fredolini, et al., Shotgun proteomics coupled tonanoparticle-based biomarker enrichment reveals a novel panel of extracellular matrix proteins as candidate serum protein biomarkers for early-stage breast cancer detection. Breast Cancer Research (2020) 22:135https://doi.org/10.1186/s13058-020-01373-9".

Gao, et al., "A latent factor model with a mixture of sparse and dense factors to model gene expression data with confounding effects." arXiv preprint arXiv:1310.4792 (Oct. 17, 2013) 1-28 Pages.

"Gao, et al., Evaluation of Serum CEA, CA19-9, CA72-4, CA125 and Ferritin as Diagnostic markers and factors of clinical parameters for colorectal cancer. Science Reports, 2018; 8:2732.".

GB2205544.6 Examination Report dated Jun. 14, 2022.

Geary et al. Identification of a Biomarker Panel for Early Detection of Lung Cancer patients. J. Proteome Res. 2019, 18, 9, 3369-3382.

Gould et al. Recent trends in the identification of incidental pulmonary nodules. Am J Respir Crit Care Med. Nov. 15, 2015;192(10):1208-14.

Graham et al. ST6GAL1: A key player in Cancer (Review). Oncol Lett. Aug. 2019; 18(2): 983-989.

(56) References Cited

OTHER PUBLICATIONS

Grossi et al. Prognostic role of the VeriStrate test in first line patients with non-small cell lung cancer treated with platinum-based chemotherapy. Lung Cancer 2018, vol. 117, pp. 64-69 (Year: 2018).
"Guinney, et al., The Consensus Molecular subtypes of colorectal cancer. Nat. Med. Nov. 2015; 21(11): 1350-1356.".
Guler et al. Detection of Early Stage Pancreatic Cancer Using 5-Hydroxymethylcytosine Signatures in Circulating Cell Free DNA. Nature Communications 11(1):5270 (Dec. 2020).
Gunther, O.P. et al. A computational pipeline for the development of multi-marker bio-signature panels and ensemble classifiers. BMC Bioinformatics 13,326 (2012), p. 1-17. (Year: 2012).
Guo et al. Deep multiple instance learning classifies subtissue locations in mass spectrometry images from tissue-level annotations. Bioinformatics, vol. 36, Issue Supplement_1, Jul. 2020, pp. i300-i308.
"Gupta, et al., Recommendations for follow-up after colonoscopy and polypectomy: a consensus update by the US multi-society task force on colorectal cancer. Gastrointest Endosc. Mar. 2020; 91(3): 463-485.".
Hadjidemetriou, et al., A novel scavenging tool for cancer biomarker discovery based on the blood-circulating nanoparticle protein corona. Biomaterials. Jan. 2019; vol. 188: pp. 118-129.
Hadjidemetriou, Liposome protein corona in vivo: from fundamental principles to a tool for cancer biomarker discovery, 2017,University of Manchester, p. 1-233 (Year: 2017).
Hamm et al. Frequent expression loss of Inter-alpha-trypsin inhibitor heavy chain (ITIH) genes in multiple human solid tumors: A systematic expression analysis. BMC Cancer, Jan. 28, 2008, 8:25; 1-15 Pages.
Hammerschmidt et al., Lung Cancer: Current Diagnosis and Treatment, 2009, Dtsch Arztebl, 106(49), p. 809-820 (Year: 2009).
Hanahan et al. Hallmarks of cancer: the next generation. Cell 144:646-674 (2011).
Haque, IS et al., Challenges in using ctDNA to achieve early detection of cancer. bioRxiv; Dec. 2017. 20 Pages; DOI: 10.1101/237578.
"Hasan, et al., Advances in pancreatic cancer biomarkers. Oncol Rev. Jan. 2019; 13(410): 69-76.".
Hasin, Yehudit, Marcus Seldin, and Aldons Lusis. "Multi-omics approaches to disease." Genome biology 18.1 (2017): 1-15. (Year:2017).
Haug U, Knudsen AB, Lansdorp-Vogelaar I, Kuntz KM. Development of new non-invasive tests for colorectal cancer screening: the relevance of information on adenoma detection. Int J Cancer. Jun. 15, 2015;136(12):2864-74. doi: 10.1002/ijc.29343. Epub Dec. 3, 2014. PMID: 25403937; PMCID: PMC4397119.
Havel et al. The evolving landscape of biomarkers for checkpoint inhibitor immunotherapy. Nat Rev Cancer 19(3):133-150 (2019).
Havlis, Jan, and Andrej Shevchenko. "Absolute quantification of proteins in solutions and in polyacrylamide gels by massspectrometry." Analytical chemistry 76.11 (2004): 3029-3036. (Year: 2004).
"Haynes, et al., Empowering multi-cohort gene expression analysis to increase reproducibility. Pac Symp Biocomput. 2016; 22: 144-153.".
Heitzer, E. et al., Current and future perspectives of liquid biopsies in genomics-driven oncology. Nat Rev Genet 20, 71-88 (2019). https://doi.org/10.1038/s41576-018-0071-5.
"Huang, et al., Emerging trends and research foci in gastrointestinal microbiome. J Transl. Med. 2019; 17(67): 1-11.".
"Siegel, et al., Cancer Statistics, 2021. CA: A Cancer Journal for Clinicians. Jan. 2021; vol. 71 Issue 1: 7-33.".
"Silvestri GA, Tanner NT, Kearney P, Vachani A, Massion PP, Porter A, Springmeyer SC, Fang KC, Midthun D, Mazzone PJ; Panoptic Trial Team. Assessment of Plasma Proteomics Biomarker's Ability to Distinguish Benign From Malignant Lung Nodules: Results of the PANOPTIC (Pulmonary Nodule Plasma Proteomic Classifier) Trial. Chest. Sep. 2018;154(3):491-500. doi: 10.1016/j.chest.2018.02.012. Epub Mar. 1, 2018. PMID: 29496499; PMCID: PMC6689113.".

"Imperiale, et al., Multitarget stool DNA testing for colorectal-cancer screening. N Engl J Med. Apr. 2014; 370:1287-1297.".
Jensen, M., and Berthold, F. Targeting the neural cell adhesion molecule in cancer. Cancer Lett., Dec. 2007., 258(1):9-21.
Jiang et al. "Surface-Enhanced Raman Nanoprobes with Embedded Standards for Quantitative Cholesterol Detection" small methods, vol. 2 Issue 11 (Nov. 13, 2018): pp. 1-14; entire document.
John, et al., "Predicting gene expression from plasma cell-free DNA using both the fragment length and fragment position." AACR Annual Meeting; Mar. 29-Apr. 3, 2019; 1 Page.
Jong et al. Selecting a classification function for class prediction with gene expression data. Bioinformatics, vol. 32, Issue 12, Jun. 15, 2016, pp. 1814-1822.
"Kampf C et al., The human liver-specific proteome defined by transcriptomics and antibody-based profiling. FASEB J. (2014) PubMed: 24648543 DOI: 10.1096/fj.14-250555".
Keshishian, et al., Multiplexed, Quantitative Workflow for Sensitive Biomarker Discovery in Plasma Yields Novel Candidates for Early Myocardial Injury. Mol Cell Proteomics. Sep. 2015;14(9):2375-93. doi: 10.1074/mcp.M114.046813. Epub Feb. 27, 2015.
Keshishian, et al., Quantitative, multiplexed workflow for deep analysis of human blood plasma and biomarker discovery by mass spectrometry. Nat Protoc. Aug. 2017;12(8):1683-1701. doi:10.1038/nprot.2017.054. Epub Jul. 27, 2017.
Khlebtsov et al. "Gap-enhanced Raman tags: fabrication, optical properties, and theranostic' applications" Theranostics, vol. 10 Issue 5 (2020): pp. 2067-2094; entire document.
Kim, et al., A chemical with proven clinical safety rescues down-syndrome-related phenotypes in through DYRK1A inhibition. Disease Models & Mechanisms (2016) 9, 839-848.
"Klein, et al., Clinical validation of a targeted methylation-based multi-cancer early detection test using an independent validation set. Annals of Oncology, 2021; vol. 32 Issue 9: 1167-1177.".
Koh, H.M., et al., Prognostic Role of S100A8 and S100A9 Protein expressions in non-small cell carcinoma of the lung. Journal of pathology and translational medicine, 2019; 53:13-22.
"Koizumi, et al., Salivary cytokine panel indicative of non-small cell lung cancer. J Int Med Res. 2018; vol. 46(9): 3570-3582.".
Lamjabbar-Alaoui et al. Lung Cancer: Biology and Treatment options. Biochimica et Biophysica Acta 2015, 1856, pp. 189-210 (Year: 2015).
Leal et al. Prognostic performance of proteomic testing in advanced non-small cell lung cancer: a systematic literature review and meta-analysis. Current Medical Research and Opinion 2020, vol. 36, No. 9, pp. 1497-1505 (Year: 2020).
Lee et al. The clinical role of VeriStrat testing in patients with advanced non-small cell lung cancer considered unfit for first-line platinum-based chemotherapy. European Journal of Cancer 2019, vol. 120, pp. 86-96 (Year: 2019).
"Li et al., PGAM1, regulated by miR-3614-5p, functions as an oncogene by activating transforming growth factor-B (TGF-B) signaling in the progression of non-small cell lung carcinoma. Cell death and Disease, 2011; 11(710): 1-16.".
Li, L. et al; "Data mining techniques for cancer detection using serum proteomic profiling", Artificial Intelligence in Medicine, vol. 32, Issue 2, 2004, pp. 71-83 (Year: 2004).
Lin, E., Lane, HY. "Machine learning and systems genomics approaches for multi-omics data." Biomark Res 5, 2 (2017), p. 1-6 (Year: 2017).
Liu et al. High expression of NFAT2 contributes to carboplatin resistance in lung cancer. Experimental and Molecular Pathology, 2019; 110:104290.
Liu, et al., Human plasma N-glycoproteome analysis by immunoaffinity subtraction, hydrazide chemistry, and mass spectrometry. J Proteome Res. Nov.-Dec. 2005;4(6):2070-80. doi: 10.1021/pr0502065.
"Liu, et al., Sensitive and specific multi-cancer detection and localization using methylation signatures in cell-free DNA. Ann Oncol. Jun. 2020; 31(6): 745-759.".
Liu et al., Spatial co-fragmentation pattern of cell-free DNA recapitulates in vivo chromatin organization and identifies tissues-of-origin. AACR. 2019; 1 Page.

(56) References Cited

OTHER PUBLICATIONS

"Lock, et al., Joint and individual variation explained (JIVE) for integrated analysis of multiple data types. Ann Appl Stat. Mar. 1, 2013;7(1):523-542. doi: 10.1214/12-AOAS597.".

Lu, et al., The crucial role of multiomic approach in cancer research and clinically relevant outcomes. EPMA Journal (2018) 9; 77-102: https://doi.org/10.1007/s13167-018-0128-8.

Lu, J., and Gu, J. Significance of β-Galactoside α2,6 Sialyltranferase 1 in Cancers. Molecules, 2015, 20, 7509-7527.

Ludwig C, Gillet L, Rosenberger G, Amon S, Collins BC, Aebersold R. Data-independent acquisition-based SWATH-MS for quantitative proteomics: a tutorial. Mol Syst Biol. Aug. 13, 2018;14(8):e8126; 1-23 Pages. doi: 10.15252/msb.20178126. PMID: 30104418; PMCID: PMC6088389.

"Luz-Crawford et al., Mesenchymal Stem Cell-Derived Interleukin 1 Receptor Antagonist Promotes Macrophage Polarization and Inhibits B Cell Differentiation. Stem Cells. Feb. 2016;34(2):483-92. doi: 10.1002/stem.2254. Epub Dec. 31, 2015. PMID: 26661518.".

Maples, et al., A highly accurate noninvasive multi-omics diagnostic test for nash. DiscernDx, Inc. Nash-Tag conference Abstract Book, Mar. 2021, p. 14.

"Massion P.P. and Walker R.C. Indeterminate pulmonary nodules: Risk for having or for developing lung cancer. Cancer Prev. Res. 2014; 7(12): 1173-1178.".

"Mathios, D., Johansen, J.S., Cristiano, S. et al. Detection and characterization of lung cancer using cell-free DNA fragmentomes. Nat Commun 12, 5060 (2021). https://doi.org/10.1038/s41467-021-24994-w".

Mazzaschi G, Facchinetti F, Missale G, Canetti D, Madeddu D, Zecca A, Veneziani M, Gelsomino F, Goldoni M, Buti S, Bordi P, Aversa F, Ardizzoni A, Quaini F, Tiseo M. The circulating pool of functionally competent NK and CD8+ cells predicts the outcome of anti-PD1 treatment in advanced NSCLC. Lung Cancer. Jan. 2019;127:153-163. doi: 10.1016/j.lungcan.2018.11.038. Epub Nov. 29, 2018. PMID: 30642544.

McDonald et al. Suspected cancer symptoms and blood test results in primary care before a diagnosis of lung cancer: a case-control study. Future Oncol. (2019) 15(33), 3755-3762.

"McGuigan A, Kelly P, Turkington RC, Jones C, Coleman HG, McCain RS. Pancreatic cancer: A review of clinical diagnosis, epidemiology, treatment and outcomes. World J Gastroenterol. Nov. 21, 2018;24(43):4846-4861. doi: 10.3748/wjg.v24.i43.4846. PMID: 30487695; PMCID: PMC6250924.".

"Meester RG, Doubeni CA, Lansdorp-Vogelaar I, Goede SL, Levin TR, Quinn VP, Ballegooijen MV, Corley DA, Zauber AG. Colorectal cancer deaths attributable to nonuse of screening in the United States. Ann Epidemiol. Mar. 2015;25(3):208-213.e1. doi: 10.1016/j.annepidem.2014.11.011. Epub Dec. 5, 2014. PMID: 25721748; PMCID: PMC4554530.".

Muller et al. Community-integrated omics links dominance of a microbial generalist to fine-tuned resource usage. Nature Communications vol. 5, Article No. 5603 (2014); 1-10 Pages.

"Murakami M, Naraba H, Tanioka T, Semmyo N, Nakatani Y, Kojima F, Ikeda T, Fueki M, Ueno A, Oh S, Kudo I. Regulation of prostaglandin E2 biosynthesis by inducible membrane-associated prostaglandin E2 synthase that acts in concert with cyclooxygenase-2. J Biol Chem. Oct. 20, 2000;275(42):32783-92. doi: 10.1074/jbc.M003505200. PMID: 10869354.".

"Nakao, et al., Oncological problems in pancreatic cancer surgery. World J Gastroenterol 2006; 12(28): 4466-4472 [PMID: 16874856 DOI: 10.3748/wjg.v12.i28.4466]".

Ocana, A., Pandiella, A. "Personalized therapies in the cancer omics era", Mol Cancer 9, 202 (2010), p. 1-12. (Year: 2010).

"Song, et al., Diagnostic and prognostic significance of serum apolipoprotein C-I in triple-negative breast cancer based on mass spectrometry. Cancer Biology & Therapy, 2016; 17(6): 635-647.".

Parimon et al. Syndecan-1 Controls Lung Tumorigenesis by Regulating miRNAs Packaged in Exosomes. Am J Pathol. 2018; 188(4): 1094-1103.

PCT/US2021/015339 International Search Report and Written Opinion dated Apr. 13, 2021.

PCT/US2022/022654 International Search Report and Written Opinion dated Aug. 15, 2022.

PCT/US2022/076297 International Search Report and Written Opinion dated Nov. 30, 2022.

"Pereira, S. P., Oldfield, L., Ney, A., Hart, P. A., Keane, M. G., Pandol, S. J., Li, D., Greenhalf, W., Jeon, C. Y., Koay, E. J., Almario, C. V., Halloran, C., Lennon, A. M., & Costello, E. (2020). Early detection of pancreatic cancer. The lancet. Gastroenterology & hepatology, 5(7), 698-710. https://doi.org/10.1016/S2468-1253(19)30416-9".

Pirinen et al. Versican in nonsmall cell lung cancer: Relation to hyaluronan, clinicopathologic factors, and prognosis. Human Pathlogy, 2004; 36(1):44-50.

Polasky, et al., Fast and comprehensive N- and O-glycoproteomics analysis with MSFragger-Glyco. Nat Methods. Nov. 2020;17(11):1125-1132. doi: 10.1038/s41592-020-0967-9. Epub Oct. 5, 2020.

Ponzi, et al., Integrative, multi-omics, analysis of blood samples improves model predictions: applications to cance. BMC Bioinformatics, 2021; 22:395; 1-17 Pages. https://doi.org/10.1186/s12859-021-04296-0.

Putcha, et al., Blood-based detection of early-stage colorectal cancer using multiomics and machine learning. Journal of clinical oncology, 2020; 38(4): 66, 3 Pages.

Qian et al. Screening for early stage lung cancer and its correlation with lung nodule detection. J Thorac Dis 2018, 1 0(Suppl 7): S846-859 (Year: 2018).

"Qu Wq, Liu L, Yu Z. Clinical value of microRNA-23a upregulation in non-small cell lung cancer. Int J Clin Exp Med. Aug. 15, 2015;8(8):13598-603. PMID: 26550300; PMCID: PMC4612985.".

Ramos-Esquivel et al., Anti-PD-1/anti-PD-L1 immunotherapy versus docetaxel for previously treated advanced non-small cell lung cancer: a systematic review and meta-analysis of randomised clinical trials. ESMO Open 2017;2:e000236; 1-11 Pages. doi: 10.1136/esmoopen-2017-000236.

Reel PS, Reel S, Pearson E, Trucco E, Jefferson E. Using machine learning approaches for multi-omics data analysis: A review. Biotechnol Adv. Jul. -Aug. 2021;49:107739; 24 Pages. doi: 10.1016/j.biotechadv.2021.107739. Epub Mar. 29, 2021. PMID: 33794304.

"Robinson, et al., A Systematic Investigation of the Malignant Functions and Diagnostic Potential of the Cancer Secretome. Cell Rep. Mar. 5, 2019; 26(10):2622-2635.e5. doi: 10.1016/j.celrep.2019.02.025.".

Roushan, et al., Peak Filtering, Peak Annotation, and Wildcard Search for Glycoproteomics. Mol Cell Proteomics. 2021;20:100011. doi: 10.1074/mcp.RA120.002260. Epub Dec. 8, 2020.

Roy et al. Multiomics data collection visualization and utilization for guiding metabolic engineering. Frontiers in bioengineering and biotechnology, 2021, 9, Article 612983; 1-13 Pages.

"Ruan H., Hu S., Zhang H., Du G., Li X., Li X., Li X. Upregulated SOX9 expression indicates worse prognosis in solid tumors: a systematic review and meta-analysis. Oncotarget. 2017; 8: 113163-113173. Retrieved from https://www.oncotarget.com/article/22635/text/".

Rubio, et al., Multi-omic analysis unveils biological pathways in peripheral immune system associated to minimal hepatic encephalopathy appearance in cirrhotic patients. Scientific Reports, 2021; 11:1907; 14 Pages. https://doi.org/10.1038/s41598-020-80941-7.

Skyarysz, A., Alkhalifah, Y., Darnley, K., Eddleston, M., McLaren, D., Nailon, W. H., Salman, D., Sykora, M., Thomas, P., & Soltoggio, A., Convolutional neural networks for automated targeted analysis of raw gas chromatography-mass spectrometry data. In Proceedings of the International Joint Conference on Neural Networks (IJCNN 2018) At: Rio de Janeiro, Brazil; 2018: 9 Pages. https://doi.org/10.1109/IJCNN.2018.8489539.

Song, M. et al; "A Review of Integrative Imputation for Multi-Omics Datasets" Front. Genet. vol. 11, article 570255, Oct. 15, 2020, p. 1-15 (Year: 2020).

St. John et al., Predicting gene expression from plasma cell-free DNA using both the fragment length and fragment position. AACR. 2019; 1 Page.

(56) References Cited

OTHER PUBLICATIONS

Stelzer, et al., The GeneCards Suite: From Gene Data Mining to Disease Genome Sequence Analyses. Curr Protoc Bioinformatics. Jun. 20, 2016;54:1.30.1-1.30.33. doi: 10.1002/cpbi.5.
Telenti, A. et al. Deep sequencing of 10,000 human genomes. Proc. Natl. Acad. Sci. USA 113(42):11901-11906 (Oct. 18, 2016).
Tenzer, S., et al. Nanoparticle size is a critical physicochemical determinant of the human blood plasma corona: a comprehensive quantitative proteomic analysis. ACS Nano 5, 7155-7167 (2011).
"The 1000 Genomes Project Consortium. A global reference for human genetic variation. Nature 526, 68-74 (2015). https://doi.org/10.1038/nature15393".
"Uhlen, M. et al., A Pathology atlas of the human cancer transcriptome. Science. 2017. PubMed: 28818916 DOI: 10.1126/science.aan2507".
Ulz, et al., Inference of transcription factor binding from cellfree DNA enables tumor subtype prediction and early detection. Nature Communications, (2019) 10:4666;1-11 Pages. https://doi.org/10.1038/s41467-019-12714-4, https://doi.org/10.1038/s41467-019-12714-4.
Unger, Klaus K., et al. "Liquid chromatography—its development and key role in life science applications." Angewandte ChemieInternational Edition 49.13 (2010): 2300-2312 (Year: 2010).
U.S. Appl. No. 17/585,303 Office Action dated Apr. 25, 2022.
U.S. Appl. No. 17/585,303 Office Action dated Jul. 18, 2022.
U.S. Serial No. 17/709, 185 Office Action dated Dec. 7, 2022.
U.S. Serial No. 17/709, 185 Office Action dated Sep. 15, 2022.
U.S. Appl. No. 17/709,202 Office Action dated Nov. 23, 2022.
U.S. Serial No. 17/720, 197 Office Action dated Jan. 5, 2023.
U.S. Serial No. 17/720, 197 Office Action dated Oct. 14, 2022.
U.S. Appl. No. 17/931,469 Office Action dated Dec. 28, 2022.
"Voronov, Elena et al. "Unique Versus Redundant Functions of IL-1α and IL-1β in the Tumor Microenvironment." Frontiers in immunology vol. 4 177. Jul. 8, 2013, doi:10.3389/fimmu.2013.00177".
Wainberg, et al., Multiomic blood correlates of genetic risk identify presymptomatic disease alterations. PNAS, Sep. 2020; vol. 117, No. 35: 21813-21820.
Wan, et al., Machine learning enables detection of early-stage colorectal cancer by whole-genome sequencing of plasma cell-free DNA. BMC Cancer (2019) 19:832; 1-10 Pages. https://doi.org/10.1186/s12885-019-6003-8.
Wang et al. MOGONET integrates multi-omics data using graph convolutional networks allowing patient classification and biomarker identification. Nature Communications, 2021; 12:3445.
Weinstein, et al. The cancer genome atlas pan-cancer analysis project. Nature genetics 45.10 (2013): 1113-1120.
"White A, Thompson TD, White MC, et al. Cancer Screening Test Use—United States, 2015. MMWR Morb Mortal Wkly Rep Mar. 2017;66(8):201-206. DOI: http://dx.doi.org/10.15585/mmwr.mm6608a1".
Xu et al. Calpain-2 Enhances non-small cell lung cancer progresion and Chemoresistance to paclitaxel via EGFR-pAKT pathway. Int J Biol Sci. 2019; 15(1): 127-137.
"Yigit M, Değirmencioğlu S, Ugurlu E, Yaren A. Effect of serum interleukin-1 receptor antagonist level on survival of patients with non-small cell lung cancer. Mol Clin Oncol. May 2017;6(5):708-712. doi: 10.3892/mco.2017.1195. Epub Mar. 15, 2017. PMID: 28515924; PMCID: PMC5431311.".
Yoon et al. NOTUM Is Involved in the Progression of Colorectal Cancer Cancer Genomics & Proteomics, 2018; 15:485-497.
Yu et al. Prognostic and clinicopathological significance of Cacna2d1 expression in epithelial ovarian cancers: a retrospective study. Am J Cancer Res 2016;6(9):2088-2097.
Yuan et al. "Antimicrobial peptide based magnetic recognition elements and Au@Ag-GO SERS tags with stable internal standards: a three in one biosensor for isolation, discrimination andkilling of multiple bacteria in whole blood" Chemical Science, vol. 9 (Nov. 2, 2018): pp. 8781-8795; entire document.

Yuan et al. Modification of α2, 6-sialylation mediates the invasiveness and tumorigenicity of non-small cell lung cancer cells in vitro and in vivo via Notch 1/Hes1/MMPs pathway. Int J Cancer. 2018; 143(9):2319-2330.
Zhang et al., Deep Learning-Based Multi-Omics Data Integration Reveals Two Prognostic Subtypes in High-Risk Neuroblastoma. Front. Genet., Oct. 18, 2018: vol. 9, Article 477; 1-9 Pages. https://doi.org/10.3389/fgene.2018.00477.
Zhang et al. Identification of Apolipoprotein C—I as a Potential Wilms' Tumor Marker after Excluding inflammatory factors. Int. J. Mol. Sci. 2014, 15(9), 16186-16195.
Zhang, et al., Phenotype Prediction using a Tensor Representation and Deep Learning from Data Independent Acquisition Mass Spectrometry. bioRxiv 2020.03.05.978635;1-11 Pages. doi: https://doi.org/10.1101/2020.03.05.978635.
Zhang et al. SMC4, which is essentially involved in lung development, is associated with lung adenocarcinoma progression. Scientific Reports, 2016, 6:34508.
"Zhang L, Zheng J, Ahmed R, Huang G, Reid J, Mandal R, Maksymuik A, Sitar DS, Tappia PS, Ramjiawan B, Joubert P, Russo A, Rolfo CD, Wishart Ds. A High-Performing Plasma Metabolite Panel for Early-Stage Lung Cancer Detection. Cancers (Basel). Mar. 7, 2020;12(3):622. doi: 10.3390/cancers12030622. PMID: 32156060; PMCID: PMC7139410.".
"Zhang S., Che D., Yang F., Chi C., Meng H., Shen J., Qi L., Liu F., Lv L., Li Y., Meng Q., Liu J., Shang L., et al.Tumor-associated macrophages promote tumor metastasis via the TGF-β/SOX9 axis in non-small cell lung cancer. Oncotarget. 2017; 8: 99801-99815. Retrieved from https://www.oncotarget.com/article/21068/text/".
Zhu et al., Apolipoprotein M promotes proliferation and invasion in non-small cell lung cancers via upregulating S1PR1 and activating the ERK1/2 and PI3K/AKT signaling pathways. Biochemical and Biophysical Research Communications, 2018, 501(2):520-526.
Dowsey, Andrew W. et al. Image Analysis Tools and Emerging Algorithms for Expression Proteomics. Proteomics 10(23):4149-4334 (2010).
Forder, Aisling. et al. Mechanisms contributing to the comorbidity of COPD and lung cancer. International Journal of Molecular Sciences 24(3):2859 1-20 (2023).
Kallback, Patrik et al. A Space Efficient Direct Access Data Compression Approach for Mass Spectrometry Imaging. Analytical Chemistry 90(6):3676-3682 (2018).
U.S. Appl. No. 18/165,264 Office Action dated Apr. 11, 2025.
U.S. Appl. No. 18/796,204 Office Action dated Apr. 10, 2025.
Chemical Abstracts Service. CAS Registry: 155887589. N-(Fmoc-N-amido-PEG4)-N-Biotin-PEG4-t-Boc-Hydrazide: pp. 1-4. STN Entry Date Apr. 22, 2021. Retrieved Nov. 4, 2024. Retrieved from URL:https://pubchem.ncbi.nlm.nih.gov/compound/155887589.
Co-pending U.S. Appl. No. 18/815,648, inventors Wilcox; Bruce et al., filed Aug. 26, 2024.
Haan, Tracie J. et al. A repeat pattern of founder events for SARS-CoV-2 variants in Alaska. medRxiv: The Preprint Server for Health Sciences :22275610, 1-17 (2022).
Hua, Serenus et al. Site-specific protein glycosylation analysis with glycan isomer differentiation. Analytical and bioanalytical chemistry 403:1291-1302 (2012).
Huo, Qun et al. A facile nanoparticle immunoassay for cancer biomarker discovery. Journal of nanobiotechnology 9(20):1-12 (2011).
Husi, Holger et al. Identification of diagnostic upper gastrointestinal cancer tissue type-specific urinary biomarkers. Biomedical Reports 10(3):165-174 (2019).
Jin, Yanxia et al. Alpha-1-antichymotrypsin as a novel biomarker for diagnosis, prognosis, and therapy prediction in human diseases. Cancer cell international 22(1):156, 1-12 (2022).
Mahmoudi, Morteza. Emerging Biomolecular Testing to Assess the Risk of Mortality from COVID-19 Infection. Molecular pharmaceutics 18(2):476-482 (2021). Published online May 20, 2020.
Monopoli, Marco P. et al. Biomolecular coronas provide the biological identity of nanosized materials. Nature nanotechnology 7(12):779-786 (2012).
Nie, Song et al. Glycoprotein biomarker panel for pancreatic cancer discovered by quantitative proteomics analysis. Journal of proteome research 13(4):1873-1884 (2014).

(56) References Cited

OTHER PUBLICATIONS

Nie, Song et al. Quantitative analysis of single amino acid variant peptides associated with pancreatic cancer in serum by an isobaric labeling quantitative method. Journal of proteome research 13(12):6058-6066 (2014).

Papi, Massimiliano, and Giulio Caracciolo. Principal component analysis of personalized biomolecular corona data for early disease detection. Nano Today 21:14-17 (2018).

PCT/US2023/067945 International Search Report and Written Opinion dated Dec. 20, 2023.

PCT/US2023/073688 International Search Report and Written Opinion dated Dec. 15, 2023.

Roberts, Andrew S. et al. Identification of potential prognostic biomarkers in patients with untreated, advanced pancreatic cancer from a phase 3 trial (Cancer and Leukemia Group B 80303). Cancer 118(2):571-578 (2012).

U.S. Serial No. 17/709, 185 Office Action dated May 17, 2024.

U.S. Appl. No. 17/709,185 Office Action dated Oct. 5, 2023.

U.S. Appl. No. 18/164,446 Office Action dated Feb. 15, 2024.

U.S. Appl. No. 18/164,446 Office Action dated Oct. 1, 2024.

U.S. Appl. No. 18/165,264 Office Action dated Sep. 5, 2024.

U.S. Appl. No. 18/643,947 Office Action dated Feb. 5, 2025.

Waks, Adrienne G. et al. Winer. Breast cancer treatment: a review. Jama 321(3):288-300 (2019).

Wu, Wenming et al. Solid serous cystadenoma of the pancreas: A case report of 2 patients revealing vimentin, β-catenin, α-1 antitrypsin, and α-1 antichymotrypsin as new immunohistochemistry staining markers. Medicine 94(12):e644, 1-4 (2015).

Yang, Yinliang et al. Cleavable trifunctional biotin reagents for protein labelling, capture and release. Chemical Communications 49(47):5366-5368 (2013).

Zacharias, Lauren G. et al. HILIC and ERLIC enrichment of glycopeptides derived from breast and brain cancer cells. Journal of proteome research 15(10):3624-3634 (2016).

Zapata, Angela et al. The role of human serum and solution chemistry in fibrinogen peptide-nanoparticle interactions. Nanoscale advances 2(6):2429-2440 (2020).

Zhu, Hongbin. et al. A LC-MS all-in-one workflow for site-specific location, identification and quantification of N-/O-glycosylation in human chorionic gonadotropin drug products. The AAPS journal 19(3):846-855 (2017).

\* cited by examiner

DIRECT CLASSIFICATION OF RAW BIOMOLECULE MEASUREMENT DATA

CROSS-REFERENCE

This application claims priority to U.S. Provisional Application No. 63/242,890, filed on Sep. 10, 2021, the content of which is incorporated herein in its entirety.

BACKGROUND

Alacritous developments in bioanalytical methodologies have generated an unmet need for large data analytics in biomolecular and omics profiling. While biological assays routinely generate gigabyte-sized datasets, many omics or mass spectrometry methods utilize small subsets of these data or processed data, focusing on readily identifiable peaks and cleanly resolved species. As variations between biological states are often evidenced by diffuse and poorly resolved biomolecules, such methods are insufficient for many forms of health and disease classification.

SUMMARY

Responsive to the need for higher accuracy omics analysis methods, the present disclosure provides a range of systems and methods for thorough biological data analysis. Rather than annotating individual features to discern high abundance biomolecules, aspects of the present disclosure provide systems and methods for raw data analysis, which, relative to annotation, may more readily utilize low intensity and overlapping features in complex datasets. Further disclosed herein are machine learning algorithms and classifiers calibrated to distinguish subtle variations within individual omics profiles, and to compare disparate features across separate datasets.

Various aspects of the present disclosure provide a system comprising: a communication interface that receives data over a communication network, the data comprising arrays of intensity values based on mass-to-charge ratios and elution times, wherein the arrays separately correspond to distinct groups of biological species of one or more biological samples; and a computer in communication with the communication interface, wherein the computer comprises one or more computer processors and computer readable medium comprising machine-executable code that, upon execution by the one or more computer processors, implements a method comprising: combining the arrays to generate a multi-dimensional image dataset by at least aligning the arrays based on identified mass spectrometry features, applying a classifier to said multi-dimensional image dataset to generate a label corresponding to a biological state.

In some aspects, the classifier is trained using contrastive learning. In some aspects, the contrastive learning comprises augmenting training datasets. In some aspects, the augmenting training datasets comprises shifting an image along said mass-to-charge ratio and/or elution time.

Various aspects of the present disclosure provide a system comprising: a communication interface that receives data over a communication network, the data comprising matrices of intensity values based on mass-to-charge ratios and elution times, where the matrices separately correspond to distinct groups of biological species of one or more biological samples; and a computer in communication with the communication interface, where the computer comprises one or more computer processors and computer readable medium comprising machine-executable code that, upon execution by the one or more computer processors, implements a method comprising: combining the matrices into a multi-dimensional dataset, applying a multi-dimensional filter to the multi-dimensional dataset to generate an output structure, and generating a label corresponding to a biological state based on the output structure. In some embodiments, the multi-dimensional filter comprises a convolutional neural network or a Siamese network.

Various aspects of the present disclosure provide a system comprising: a communication interface that receives data over a communication network, the data comprising datasets that separately correspond to distinct groups of biological species of one or more biological samples; and a computer in communication with the communication interface, wherein the computer comprises one or more computer processors and computer readable medium comprising machine-executable code that, upon execution by the one or more computer processors, implements a method comprising: combining the datasets into a multi-dimensional dataset, applying a convolutional neural network to the multi-dimensional dataset to generate a label corresponding to a biological state based on the output structure. In some embodiments, the multi-dimensional filter separately acts upon individual arrays of the multi-dimensional dataset. In some embodiments, the multi-dimensional filter performs a transform which utilizes data from a plurality of arrays of the multi-dimensional dataset.

Various aspects of the present disclosure provide a method comprising: receiving data comprising arrays of intensity values based on mass-to-charge ratios and elution times, wherein the arrays separately correspond to distinct groups of biological species of one or more biological samples; combining the arrays into a multi-dimensional dataset; applying a multi-dimensional filter to the multi-dimensional dataset to generate an output structure; and generating a label corresponding to a biological state based on the output structure.

Various aspects of the present disclosure provide a method comprising: receiving data comprising datasets that separately correspond to distinct groups of biological species of one or more biological samples; combining the datasets into a multi-dimensional dataset; and applying a convolutional neural network to the multi-dimensional dataset to generate a label corresponding to a biological state based on the output structure.

Various aspects of the present disclosure provide a computer-implemented method of training a neural network for detection of a biological state from raw mass spectrometry data. The method may include collecting a first set of digital images from a database. The first set of digital images may comprise raw mass spectrometry data generated from subjects having a disease state. The method may include applying one or more transformations to each digital image of the first set of digital images, including mirroring, rotating, smoothing, or contrast reduction to create a modified set of digital images. The method may include creating a first training set comprising the collected first set of digital images, the modified set of digital images, and a second set of digital images comprising raw mass spectrometry data generated from subjects not having the disease state. The method may include training the neural network in a first stage using the first training set. The method may include creating a second training set for a second stage of training comprising the first training set and digital images of raw mass spectrometry data generated from subjects not having the disease state and that are incorrectly detected as generated from subjects having the disease state after the first stage of training. The method may include training the neural network in a second stage using the second training set.

In some embodiments, the convolutional neural network generates the label by applying a filter to the multi-dimensional dataset to generate an output structure, and generates the label from the output structure. In some embodiments, the datasets comprise matrices of intensity values based on mass-to-charge ratios and elution times. In some embodiments, the multi-dimensional dataset comprises a higher dimensionality than any one of the arrays. In some embodiments, the multi-dimensional dataset comprises a hyperspectral data cube. In some embodiments, the multi-dimensional dataset comprises an image, or where the arrays comprise images.

In some embodiments, the convolutional neural network comprises features corresponding to m/z ratios and elution times. In some embodiments, the convolutional neural network generates the label based on a subset of the features.

In some embodiments, the intensity values relate to abundances of the biological species. In some embodiments, the intensity values based on mass-to-charge ratios and elution times are generated by mass spectrometry. In some embodiments, the biological species are ionized by a system or method comprising a chemical ionization, plasma and glow discharge, electron impact, electrospray ionization, fast-atom bombardment, field ionization, laser ionization, matrix-assisted laser desorption ionization, plasma-desorption ionization, resonance ionization, secondary ionization, spark source, or thermal ionization. In some embodiments, the one or more biological samples are enriched for the distinct groups of biological species. In some embodiments, the distinct groups of biological species comprise proteins, lipids, metabolites, nucleic acids, or a combination thereof.

In some embodiments, the distinct groups of biological species comprise biomolecules adsorbed to physiochemically distinct groups of particles. In some embodiments, the particles comprise nanoparticles. In some embodiments, the particles comprise a metal, a polymer, a lipid, or a combination thereof. In some embodiments, the physiochemically distinct groups of particles comprise particles comprising distinct surface characteristics. In some embodiments, the distinct surface characteristics comprise distinct charges or hydrophobicities.

In some embodiments, the one or more biological samples comprise a biofluid sample. In some embodiments, the biofluid sample comprises a blood sample, a plasma sample, or a serum sample. In some embodiments, the biological state comprises a healthy state or a disease state. In some embodiments, the system further comprises an output device that outputs the label corresponding to the biological state, or outputs a recommendation regarding treating the subject based on the biological state. In some embodiments, the subject comprises a mammal. In some embodiments, the subject comprises a human.

DETAILED DESCRIPTION a. Introduction

Figure 1:
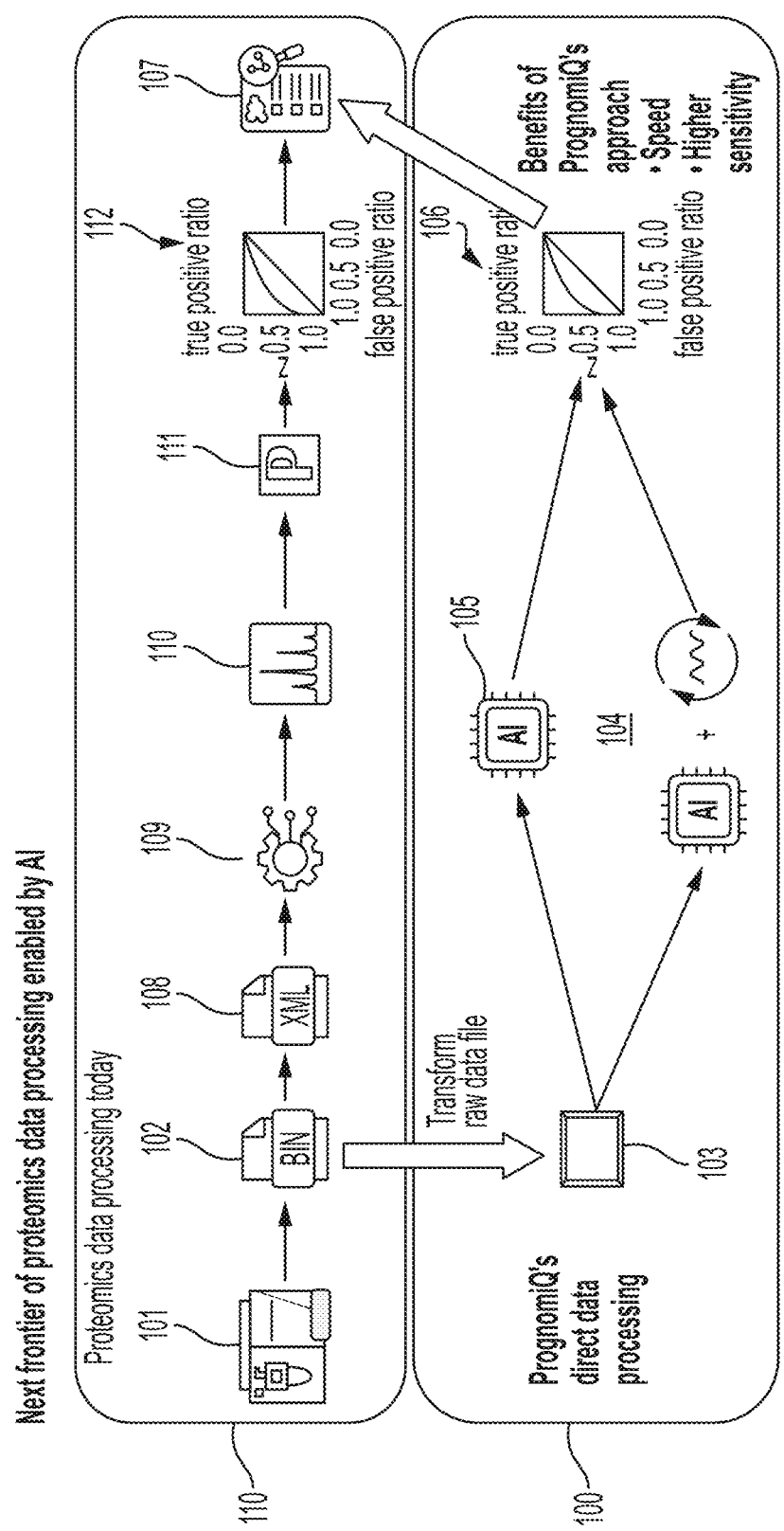
FIG. 1 provides a schematic overview of a method consistent with the present disclosure, as well as a method which relies on data annotation for comparison.

Aspects of the present disclosure provide computer implemented systems for analyzing complex data for biological state determinations. In some cases, methods and systems herein may be applied to proteomics which is an important step to fill the gap of knowledge between genomic and metabolic states of living organisms, potentially leading to a discovery of novel biomarkers to diagnose human diseases.

Conventional mass spectrometry procedures for proteomics typically include steps that 1) break down a protein of a large molecular weight into small peptides (precursor ions) and 2) record a signal from each precursor based on the ion's electrokinetic behavior. The recorded signal is then interpreted by a computer algorithm (e.g., peak-peaking), that produces a list of physicochemical features of the precursor ion, including mass-charge ratio, ion mobility, retention time, and a signal intensity. Lastly, given the mass spectroscopy features information, a peptide (amino acid sequence) is inferred by comparing them to a features library of previously known peptides ("database search") or by sorting the most probable sequence among the peptide candidates ("de novo sequencing"). This disclosure improves upon conventional mass spectrometry methods and data classification by omitting certain aspects, or simply bypassing some of these steps entirely.

Further, while experimental methods often generate large quantities of data, many analysis methods interrogate limited portions of these data (e.g., individual datapoints or narrow feature spaces) to characterize samples, thereby discarding the majority of information available for analysis. For example, while liquid chromatography-mass spectrometry (LC-MS) can generate spectra with hundreds of thousands of features, LC-MS-based health classification methods often select small subsets of datapoints to identify individual biomarkers, thus ignoring the majority of the information contained in LC-MS spectra. As many diseases are evidenced by minor homeostatic shifts, such methods are unable to detect a range of common diseases, let alone subtle progressions towards disease states. On the other hand, the methods disclosed herein enable use of data points that are otherwise thrown out in the wash, if you will, when they do not align with a known and well-characterized feature.

For instance, other methods may apply a deep learning-based approach to mass spectrometry analysis, but it is used in the other methods only to identify features into a protein group, or to distinguish a real signal indicating a peptide from noise among mass spectrometry features. It remains challenging to identify novel peptide features relevant to human disease models because the disease-relevant biomarkers can exist in a low abundance, immersed in noise signals, or stochastically present within a group of samples which are usually discarded in the conventional methods.

Deep omics analysis, as presented in embodiments of this application, differs from the above approaches by utilizing full or extensive portions of the raw biological datasets to discern biological state information. Rather than focusing on individual datapoints or narrow windows (for example by selecting a subset of peaks from a mass spectrum), the computer implemented systems of the present disclosure profile extensive feature spaces, and can increase the dimensionality of biological data sets by comparing disparate features both within and across datasets.

In an aspect of the present disclosure, a deep learning-based classifier is provided to discriminate a set of mass spectrometry features given a disease or control models. The present disclosure beneficially provides an improved deep learning network that is capable of training the deep learning-based classifier with limited training datasets while maintaining high performance. In some cases, labeled training data can be sparse and insufficient training data can result in poor performance of a model, but methods and systems herein may train a neural network with limited label data by employing a contrastive learning, a self-supervised method that learns the input features without requiring labels information. For example, the neural network may be trained through an image augmentation and generally without sample labels, where only a last fully connected layer is trained with the labels. This beneficially allows for avoiding issue typically associated with limited clinical samples sizes (e.g., when there are about 200 samples or less) and taking advantage of a rich information contained in each data to learn the representations.

As an aspect of some processes described herein, a computer implemented system of the present disclosure may utilize unannotated data for biological state analysis. Other aspects of this application, also differ from previous approaches by utilizing individual windows of the raw datasets but without processing the raw data into peaks and annotating individual biomolecules. Such aspects may enable rapid, efficient data processing which may be performed on-site for data classification.

As used herein, data annotation can denote labeling or associating data features (e.g., peaks in LC-MS data) with specific species (e.g., biomolecules). In spite of the fact that data annotation typically results in a loss of information, many classification methods utilize annotated biological data to identify individual biomarkers in samples. For example, LC-MS-based classification methods often convert hundreds of thousands of signals into relative abundances for tens of biomolecules prior to making biological state determinations. While such methods can be effective in limited applications, they more often are inherently limited in terms of accuracy, utility, and scope.

Central among these issues, analysis with annotated data (e.g., with biomolecule-level identifications) often focus solely on changes associated with identified analytes. Many biomolecules are either not identifiable or uniquely identifiable (e.g., one of a number of proteins or other biomolecules associated with overlapping datapoints), and therefore tend to not contribute to such analysis. Furthermore, the profile of a data feature, such as an asymmetry of a chromatographic peak, may include information which is lost during data annotation.

Additionally, datapoints which are insufficient for annotation using previous methods (e.g., too low of signal or unsuitable for tandem mass spectrometric analysis) may nonetheless comprise information useful for disease classification using the present methods. For example, in a lipidomic mass spectrometric experiment, phosphatidylcholines can appear as a broad set of overlapping bands. While individual peaks within this band are often unassignable, the relative intensities and isotopic patterns of peaks within a phosphatidylcholine band may reveal information regarding the biological state of a subject or sample.

In many aspects, the present disclosure provides computer-implemented systems for analyzing unannotated data for biological state classification and analysis. Contrasting with many conventional classification methods, the present disclosure provides analytics workflows which utilize entire or substantial portions of biological datasets, greatly increasing the amount of information which can be derived from experimental data. The unannotated data may be raw. For example, the unannotated data may be an array or matrix of intensity values based on mass-to-charge ratios and elution times derived from an LC-MS experiment. The data may be processed such as Fourier transformed and baseline corrected nuclear magnetic resonance (NMR) data.

The methods described herein may use object recognition software or image recognition software to identify a dataset as having features indicative of a biological state. For instance, dataset may be converted to an image, or may be input into an object or image recognition software directly as an array or matrix of data. Various aspects of object or image recognition software may be used, such as aspects used to detect lines, curves, or other features of an image. The array or matrix may comprise data or measurements corresponding to distinct biological species, or to distinct sets of a biological species obtained through separate methodologies.

Some aspects include applying a classifier to the data, while some aspects include training the classifier. The methods described herein may be used to predict or identify a disease state or other biological state. the classifier may be trained to predict or identify the disease state or other biological state, and an output of the classifier may include data indicative of a disease state. A classifier may be used to predict or identify the disease state or other biological state by applying the classifier to the data. A disease state may include a disease or disorder such as cancer.

Some methods include alignment of mass spectrometry features that include feature information of precursor ions (MS1), conversion of MS1 features into an image or pseudoimage, and/or performing contrastive learning with a neural network. Some aspects include applying the neural network to identify a sample as indicative of a state such as a biological or disease state, or for distinguishing between two or more states.

b. Computer-Implemented Methods and Systems

Described herein are system. The system may be computer-implemented. The system may include: a communication interface that receives data over a communication network; and a computer in communication with the communication interface, where the computer comprises one or more computer processors and computer readable medium comprising machine-executable code that, upon execution by the one or more computer processors, implements a method. In some cases, the data correspond to distinct groups of biological species of one or more biological samples. In some cases, the data include an array or a plurality of arrays. An array may include a matrix.

In some cases, the data comprises an array. The data may comprise a 1-dimensional (1D) array (e.g., a vector), a 2-dimensional (2D) array (e.g., a matrix), a 3-dimensional (3D) array, or a 4-dimensional (4D) or higher-dimensional array. The array may comprise LC-MS data, gas chromatography-mass spectrometry (GC-MS) data, direct injection mass spectrometry data, NMR data, light absorbance data (e.g., infrared light absorbance data, ultraviolet-visible light absorbance data, X-ray absorbance data), light scattering data (e.g., Raman or resonance Raman), imaging data, fluorescence data, sequencing data (e.g., peptide nanopore sequencing data), or a combination thereof.

The data may include measurements acquired by a mass spectrometer. The data may include intensity values. The data may be represented as an image, or as an array or matrix. In some cases, the data comprises an array of intensity values. For example, the data may be based on mass-to-charge (m/z) ratios and elution times of LC-MS and/or GC-MS data. In some cases, the array (or matrix) may be two-dimensional including rows and columns. The array (or matrix) may include an x axis and a y axis, where one axis (x or y) comprises m/z ratios, and the other axis (x or y) comprises time (such as retention time or elution time). A computer may package the data (which may be represented as an array or matrix) simply as packets of information that include an intensity value, a m/z ratio, and a time such as an elution, where the data include intensity values corresponding to a variety of m/z ratios and times.

In some cases, the datasets may be generated from samples enriched with different particles. For example, a first dataset may comprise LC-MS data of biomolecules enriched from a human plasma sample by adsorption to a polystyrene particle, a second dataset may comprise LC-MS data of biomolecules enriched from the human plasma sample by adsorption to a polyacrylate particle, and a third dataset may comprise LC-MS data of biomolecules enriched from the human plasma sample by adsorption to a chitosan nanoparticle.

The data may comprise multiple arrays. For example, the data may comprise a plurality of arrays which correspond to distinct groups of biological species of one or more biological samples. In some cases, the data comprise an array of proteomic data, an array of lipidomic data, an array of metabolomic data, an array comprising genomic data, an array comprising transcriptomic data, an array comprising epigenomics data, an array comprising glycomics data, or an array comprising secretomics data, or any combination thereof (for example, multiple arrays). In some cases, the data comprise an array of proteomic data, an array of lipidomic data, and an array of metabolomic data. In some cases, the data comprise at least two arrays which correspond to distinct groups of biological species, at least three arrays which correspond to distinct groups of biological species, at least four arrays which correspond to distinct groups of biological species, at least five arrays which correspond to distinct groups of biological species, or at least six arrays which correspond to distinct groups of biological species.

Distinct groups of biological species may include, for example, different types of biomolecules. Different types of biomolecules may include, for example, a first type of biomolecule including proteins, and another type of biomolecule such as lipids or metabolites. In some cases, distinct groups of biological species may include different groups of the same type of biomolecule. For example, distinct groups of biological species may include distinct groups of proteins.

In some cases, the data comprise a plurality of arrays corresponding to biomolecules collected on different particles. As biomolecule adsorption to particles depends not only on particle physicochemical properties, but on sample composition and conditions (e.g., pH and viscosity), variations in adsorbed biomolecule (hereinafter biomolecule corona) profiles across multiple particle types can comprise an abundance of information utilizable for biological state determination. Accordingly, in some cases, the data comprise at least two arrays which correspond to distinct particle types contacted to a biological sample, at least three arrays which correspond to distinct particle types contacted to a biological sample, at least four arrays which correspond to distinct particle types contacted to a biological sample, at least five arrays which correspond to distinct particle types contacted to a biological sample, or at least at least six arrays which correspond to distinct particle types contacted to a biological sample.

In some cases, the method implemented by the one or more computer processors comprises combining (e.g., concatenating) at least a portion of the data into a multi-dimensional dataset. This may comprise combining multiple arrays to form a higher dimensional array (e.g., combining 1D arrays to form a 2D, 3D, 4D, or 5D array). For example, the data may comprise arrays of intensity values based on mass-to-charge ratios and elution times, the arrays separately corresponding to distinct groups of biological species of one or more biological samples, and the method implemented by the one or more computer processors may comprise combining the arrays into a multi-dimensional dataset.

The method implemented by the one or more computer processors may comprise a filter. The filter may modify data to transform the data into an output structure. In some cases, the output structure may be a standard structure (e.g., with predetermined dimension or data format) that is suitable for analysis by a neural network. For example, the filter may sharpen peaks or remove false-peaks (e.g., peaks arising from noise) in LC-MS and GC-MS data to generate output structures more suitable for analysis by a neural network. The filter may act upon an individual dataset of the data (e.g., a single array of a multi-dimensional dataset comprised of multiple arrays), thereby utilizing data only from the individual dataset to modify the individual dataset. The filter may act upon multiple datasets of the data (e.g., multiple arrays of a multi-dimensional dataset comprised of multiple arrays), thereby utilizing information derived across multiple datasets to transform the data of an individual dataset into the output structure. For example, a filter may modify data within a proteomic dataset in part based on data within a separate lipidomic dataset. A filter may modify a dimension of an input dataset. For example, a filter may compress a 3D array into a 2D or a 1D array, or compress multiple 2D arrays into a single 2D array. The method implemented by the one or more computer processors may comprise a plurality of filters. Two filters of the plurality of filters may act upon a dataset in sequence or in parallel. A filter may accept (e.g., combine) multiple output structures as input. A plurality of filters may generate a plurality of output structures for analysis by the system.

The method implemented by the one or more computer processors may comprise analyzing individual datasets (e.g., a single array), the multi-dimensional dataset, an output structure generated by applying a filter to a dataset or to a multi-dimensional dataset, or any combination thereof. The analyzing method may be performed by a neural network. For example, a method described herein, or a computer system may comprise applying a neural network. The analyzing may generate a label corresponding to a biological state of one or more biological samples to which the datasets correspond. The label may identify a health or disease status of the sample, for example that a tissue biopsy sample comprises a form of cancer. The label may identify a health or disease stage of the sample, for example that a donor of a blood sample has cancer at an early stage. An example of a method consistent with the present disclosure may comprise (a) generating separate lipid, metabolite, and protein LC-MS data from a whole blood sample from a single subject; (b) receiving the data by a communication interface from a communication network; (c) implementing a method with a computer in communication with the communication interface, the method comprising: (i) combining the lipid, metabolite, and protein LC-MS data into a multi-dimensional dataset; (ii) applying a multi-dimensional filter to the multi-dimensional dataset to generate an output structure; and (iii) identifying the single subject as likely to have cancer based on the output structure.

A computer-implemented method consistent with the present disclosure may comprise training or applying a classifier. The classifier may include a convolutional neural network. In some aspects, the classifier includes a Siamese network. For example, some aspects include a system comprising: a communication interface that receives data over a communication network, the data comprising datasets that separately correspond to distinct groups of biological species of one or more biological samples; and a computer in communication with the communication interface, where the computer comprises one or more computer processors and computer readable medium comprising machine-executable code that, upon execution by the one or more computer processors, implements a method comprising: (a) combining the datasets into a multi-dimensional dataset, and (b) applying a convolutional neural network to the multi-dimensional dataset to generate a label corresponding to a biological state based on the output structure. The convolutional neural network may apply a filter or a plurality of filters to the datasets and/or multi-dimensional dataset to generate one or more output structures, and may generate the label from the output structure. The filter or plurality of filters may accentuate differences between qualitatively similar datasets, such as by selectively enlarging and shrinking peaks based on classification utility. As an example, in tandem lipidomic and proteomic LC-MS data analysis, a filter may enlarge peaks within a phosphatidylcholine window of the lipidomic LC-MS data if peaks corresponding to interleukin-10 family cytokines are present in the proteomic LC-MS data, and diminish peaks within the phosphatidylcholine window of the lipidomic LC-MS data if peaks corresponding to interleukin-10 family cytokines are absent in the proteomic LC-MS data.

A dataset may comprise matrices of intensity values based on mass-to-charge ratios and elution times. The intensity values may be generated by mass spectrometry. For example, the datasets may comprise 2D arrays of LC-MS and GC-MS data. The datasets may comprise identical types of data (e.g., each dataset may comprise LC-MS data). The datasets may comprise samples enriched with different particles.

Some prior methods use neural networks to perform object detection. A neural network may include a framework of machine learning algorithms that work together to classify inputs based on a previous training process. In object detection, a neural network may classify images as either containing an object or not, based upon the model being previously trained on a set of images. Some aspects include the use of object detection software, or a neural network in image detection of raw mass spectrometry data. For example, in comparing an image of raw mass spectrometry data from a person suspected of having a disease to images or features from raw mass spectrometry data of subjects with and without the disease state.

In some aspects, object recognition software suffers from the inability to robustly detect relevant features in images where there are shifts, distortions, and variations in scale and rotation in the image. This issue may be addressed by using a combination of features to more robustly detect relevant features such as features present in images of raw mass spectrometry data from healthy subjects but not from diseased subjects, or vice versa. Some aspects include use of an expanded training set of images to train the neural network. This expanded training set may be developed by applying mathematical transformation functions on an acquired set of images generated from raw mass spectrometry data. These transformations can include affine transformations, for example, rotating, shifting, or mirroring or filtering transformations, for example, smoothing or contrast reduction. The neural networks may then be trained with this expanded training set using stochastic learning with backpropagation which is a type of machine learning algorithm that uses the gradient of a mathematical loss function to adjust the weights of the network. The introduction of an expanded training set may increase false positives when classifying images of raw mass spectrometry data generated from subjects with a healthy disease state. Accordingly, some aspects include minimization of these false positives by performing an iterative training algorithm, in which the system is retrained with an updated training set containing the false positives produced after image detection has been performed on a set of images of raw mass spectrometry data generated from healthy subjects. This combination of features may provide a robust disease detection model that can detect disease while limiting the number of false positives in mass spectrometry images.

FIG. 1 provides a schematic overview of a method consistent with the present disclosure 300, along with a comparison to a method which relies on data annotation 110. In this example, both methods utilize mass spectrometric data. A mass spectrometer 101 generates a raw data file 102 (e.g. a BIN file) readable by a computer executable medium. The method consistent with the present disclosure can utilize direct data processing. This may include converting the data file 102 into an image 103 (or other array format) such as an LC-MS spectrum. In some aspects, the array comprises a multi-channel, color-coded fluorescence imaging spectrum. The raw data file may be subjected to direct analysis 104 (e.g. direct detection of a disease or biological state), for example by a convolutional neural network, and may optionally, in parallel, be partially or fully annotated 105 (e.g. with peptide IDs). The data may or an output by the convolutional neural network be input into a statistical model 106, which generates a classification 107 such as a biological state determination.

FIG. 1 also outlines a method for annotated data analysis 110, which is more cumbersome, includes the use of more computer power and processing to perform, and also may result in less accurate classification than the direct classification method. The method that uses annotated data may include transforming or converting 108 the raw data file 102 to generate a spectrometric data file, processing 109 the spectrometric data file and applying a detection algorithm 110 to generate data annotations 111 (e.g. peptide IDs). The annotated data may be input into a trained classifier, which generates a classification 107. Relative to the method consistent with the present disclosure 110, the method for annotated data analysis 100 can be limited to biological state determinations evidenced by annotatable data features.

Some aspects relate to proteomic data classification. For example, a method may include comprising: obtaining raw data comprising mass-to-charge ratio ratios and elution times; generating a data matrix from the raw data; and applying a classifier to the data matrix to assign a label corresponding to a biologic state to the data matrix, where the classifier is trained using data matrices generated from training data comprising mass-to-charge ratio ratios and elution times. The data matrix may include rows and columns corresponding to the mass-to-charge ratio ratios and elution times. The data matrix comprises an image representative of the rows and columns. Applying the classifier to the data matrix to assign a label corresponding to a biologic state to the data matrix may include identifying a region of the data matrix useful for identifying a biological state, and assigning the label based on mass-to-charge ratio ratios and elution times represented in the region.

Figure 2A:
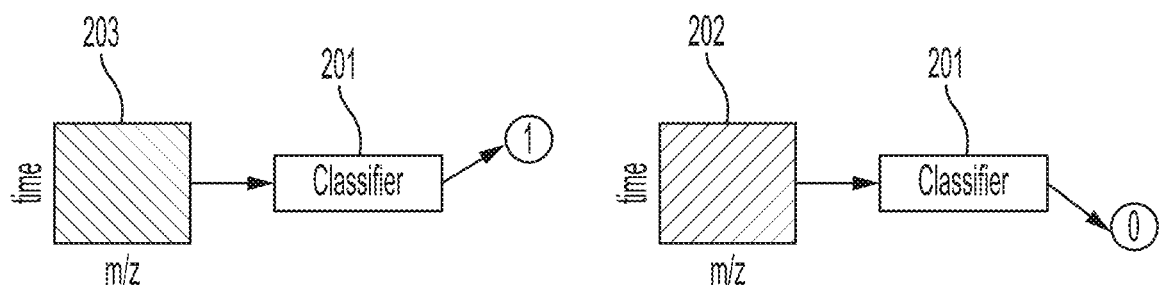
FIG. 2A illustrates aspects of training a classifier with data from healthy subjects and with data from subjects having a disease state.
Figure 2B:
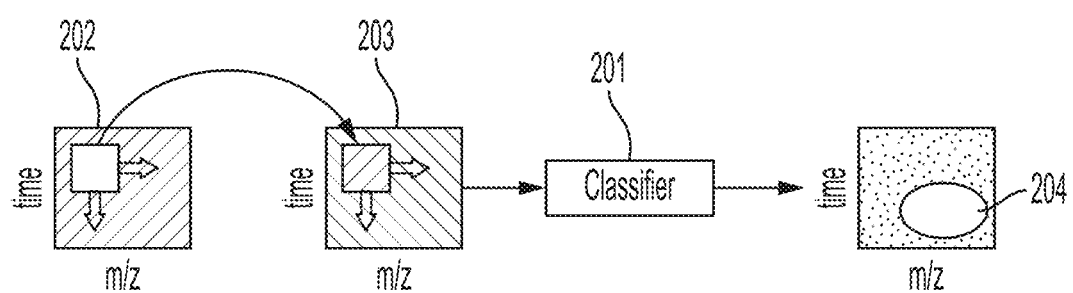
FIG. 2B illustrates aspects of training a classifier to distinguish data from healthy subjects versus data from subjects having a disease state.

FIG. 2A-2B illustrate a method for training a classifier to distinguish healthy subjects from subjects with a disease state such as cancer. The method may include tiled image swapping, and may be used for discovering biomarkers by training on raw mass spec data. Step 1 may include training a classifier to distinguish between raw mass-spec MS1 data from cancer and healthy samples. As outlined in FIG. 2A, a classifier 201 is trained with data from healthy subjects 202 and data from subjects with cancer 203, such that the classifier is able to accurately distinguish samples of these two types. The data may be raw and unannotated, for example unprocessed LC-MS or GC-MS data. The data may be provided as an array (e.g., as a matrix or an image).

In Step 2, the classifier output may be recorded by presenting data where tiles in cancer samples have been swapped with corresponding ones from healthy samples, and tiles may be swept across the entire image or data set. As depicted in FIG. 2B, the classifier is provided mixed inputs 204 generated by swapping regions from healthy and cancer data. The classifier output 205 is recorded, and regions where differences appear are identified as potentially useful for classifying between the healthy state and the disease state. These regions may include identifiable biomarkers (e.g. a known protein), or may be useful according to the methods disclosed herein without including an identifiable biomarker. Instead of binary classifiers, networks which predict similarity (e.g. Siamese networks) may also be used.

Figure 2C:
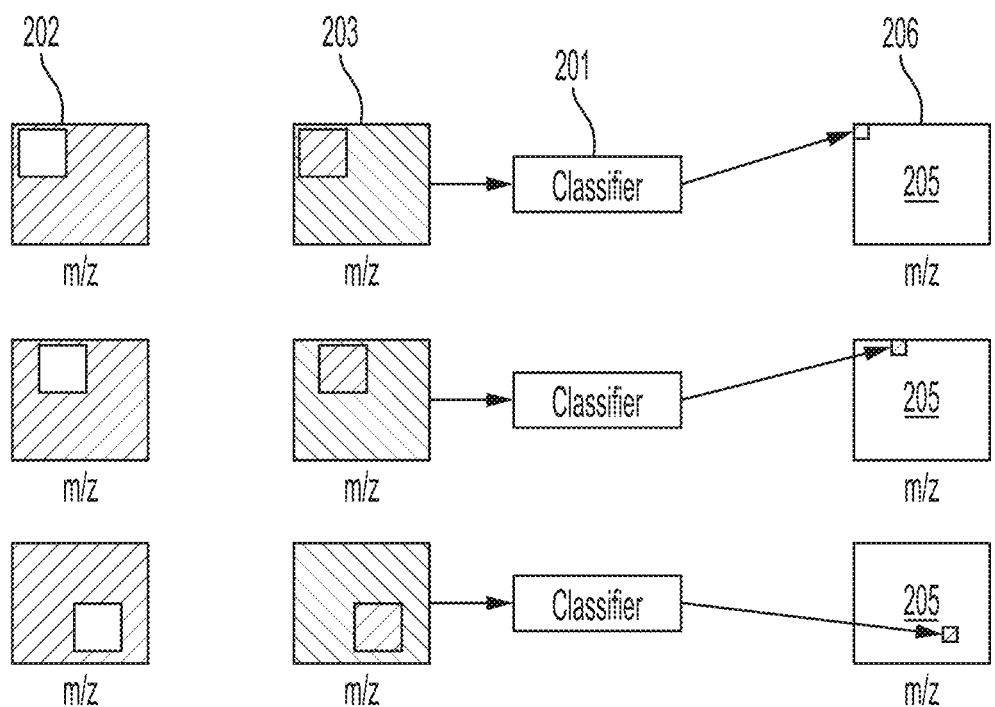
FIG. 2C illustrates aspects of training a classifier to distinguish data from healthy subjects versus data from subjects having a disease state, and generating an output to be used for classification.

As shown in FIG. 2C, this process is iterated over multiple regions of the cancer and healthy data, in each case swapping different portions of the cancer data for healthy data. Images may be formed from classifier outputs. From each output, features and regions identified as potentially useful for distinguishing between healthy or cancer samples are recorded in a classifier image 206. Images are formed from all healthy vs cancer pairs and then aggregated (e.g. mean or median). The tiling approach filters non-useful features from the classifier to generate a classifier image 206 with features which distinguish healthy from cancer samples, and lacking features which do not aid in classification. Once completed, the classifier image 206 may be used to distinguish samples of unidentified cancer status.

A method described herein may include parallelized data analysis. Such methods may include combined data analysis executable by computer-implemented systems. While parallelized data analysis methods as disclosed herein can enhance processing rate (e.g., by a computer processing unit), they can also enhance classification utility by identifying important correlations across distinct datasets. The images in FIG. 2A-2C include different shades of gray to represent cancer data and healthy data, but the data used by a classifier may include mass spectrometry data such that m/z is represented by the x axis, elution time is represented by the y axis, and ion intensity values on a z-axis.

Figure 3A:
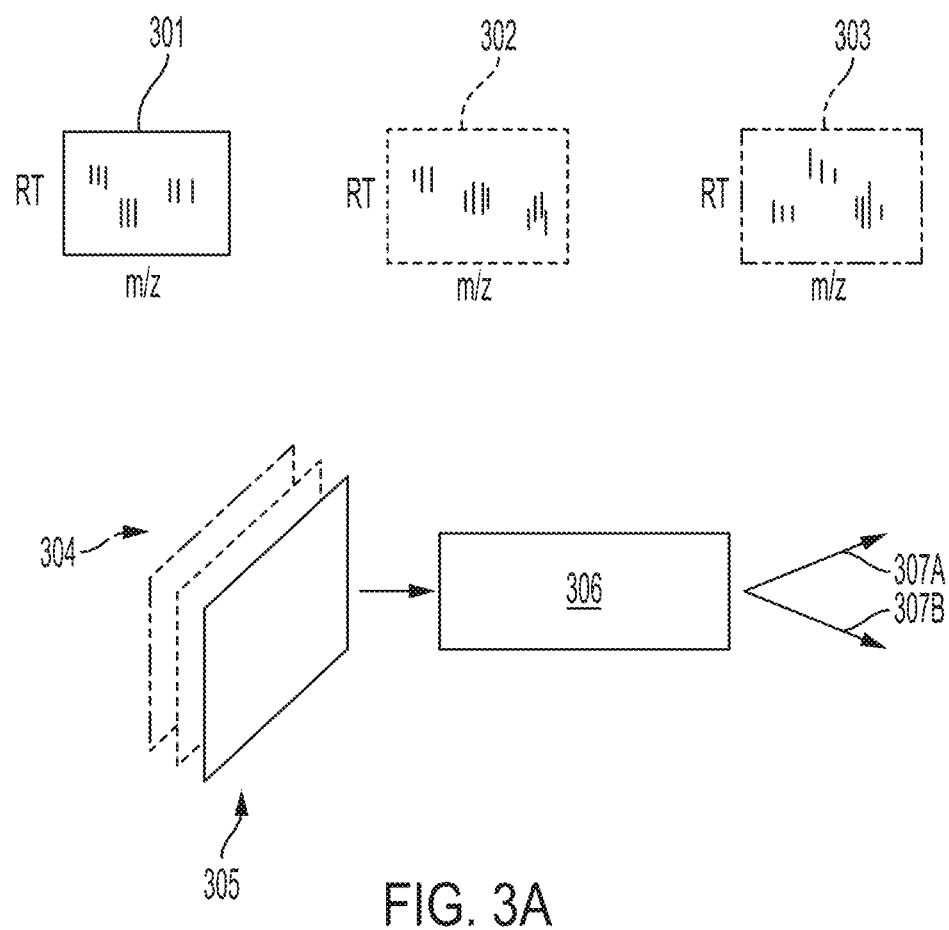
FIG. 3A illustrates a method for parallelized data processing using measurements of different of types of biomolecules.

Some aspects relate to direct detection of a biological state (e.g. a disease state such as cancer, or a healthy state) with mass spectrometry multi-omic data. For example, a method may include (1) creating a hyperspectral data cube where proteomics, lipidomics and metabolomics spectra are the three channels (e.g. red, green, blue [RGB] channels); and (2) training a convolutional neural network with 3 dimensional kernels to directly classify the hyperspectral data cube as indicative of the biological state. FIG. 3A outlines a general method for parallelized data processing. In a first step, multiple datasets (e.g. proteomic data 301, lipidomic data 302, and metabolomic data 303) are combined 304 to generate a multi-dimensional dataset 305. The datasets 301-303 may contain the same type of data (e.g., all datasets may be LC-MS data), or of different types of data (e.g., one dataset is LC-MS data, one dataset is GC-MS data, one dataset is NMR data). The datasets may correspond to different samples, timepoints (e.g., separate plasma samples collected from a single subject over monthly intervals), biomolecule types (e.g., proteins, lipids, and metabolites), or assay parameters (e.g., different particle types used to collect biomolecules from a single sample).

The datasets 301-303 are combined 304 to form a multi-dimensional dataset 305. This process may comprise concatenation, such that the dimensionality of the multi-dimensional dataset 305 is equal to or less than the highest dimensionality dataset (301, 302, or 303), or may comprise stacking, such that the multi-dimensional dataset 305 comprises a higher dimensionality than the highest dimensional dataset (301, 302, or 303). For example, if the datasets 301-303 are each 3-dimensional arrays, they may be concatenated to form a single 2-dimensional multi-dimensional dataset 305, or they may be stacked to generate a 4-dimensional multi-dimensional dataset 305 (e.g., a hypercube). Any number of datasets 301-303 may be combined 304 to form the multi-dimensional dataset 305.

A classifier 306 (e.g. a 3-dimensional convolutional neural network) is applied to the multi-dimensional dataset 305 to generate a final output (e.g. 0 [healthy] 307A or 1 [cancer] 307B). The trained classifier may separately analyze each dataset of the multi-dimensional dataset 305, or may perform combined analysis which compares or transforms data features of two or more of the constituent datasets 301-303. For example, the trained classifier 306 may comprise a convolutional neural network which separately filters and analyzes each constituent dataset 301-303 of the multi-dimensional array, and combines output from each analysis to generate a final output 307A or 307B. Alternatively, the trained classifier 306 may comprise a 3-dimensional convolutional neural network with kernels which simultaneously utilizes data from multiple (e.g., all) constituent datasets 301-303 of the multi-dimensional dataset 305 to generate outputs. The trained classifier 306 may be configured to generate a plurality of different final outputs 307A or 307B, for example body mass index values spanning from 12 to 45 in single unit increments. The final output 307A or 307B may be a biological state, such as healthy or cancerous.

Figure 3B:
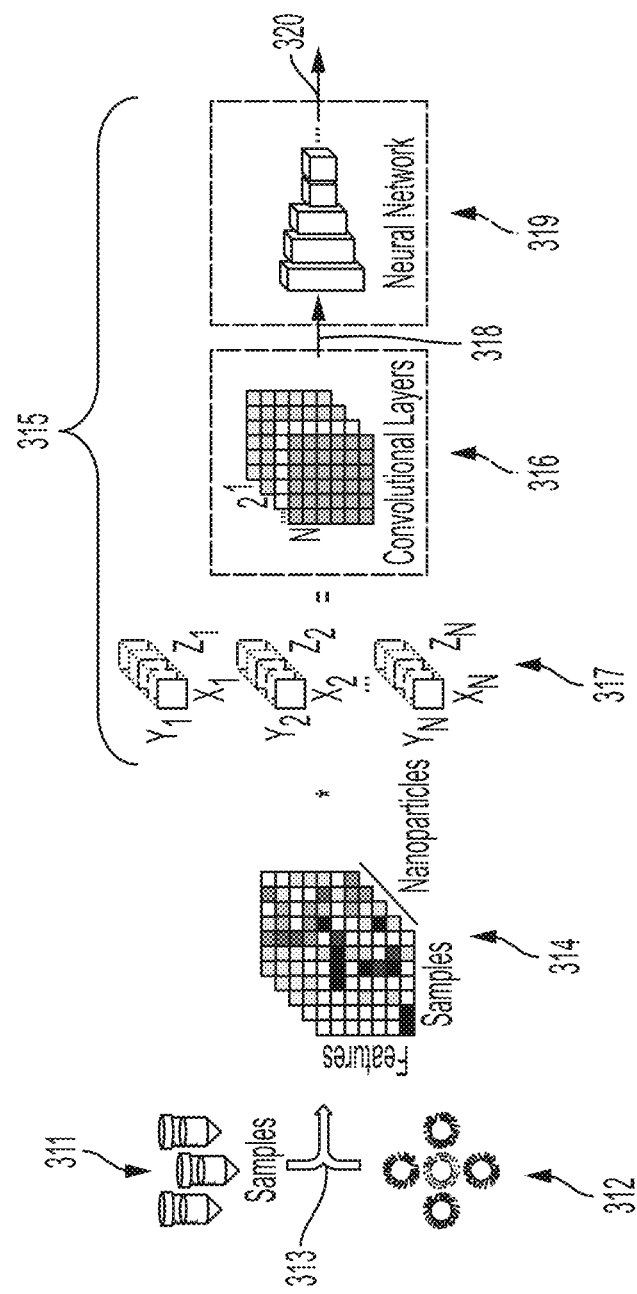
FIG. 3B illustrates a method for parallelized data processing using measurements of biomolecules adsorbed to distinct types of particles.

A method described herein may include applying a convolutional neural network classifier to data obtained using particles. The data (e.g. including separate datasets for biomolecules adsorbed to separate nanoparticles) may be analyzed in parallel as outlined in FIG. 3B. In some cases, biological samples processed and assayed using the nanoparticle platform to result in quantified features per sample per nanoparticle. The quantities can be represented as arrays (e.g. in matrix form as features×samples) per nanoparticle. One or more convolutional kernels can then be applied over each matrix and the outputs from these operations (e.g. convolutional layers) can subsequently feed into a neural network model for different predictive tasks such as biological state classification. Multiple samples 311 (e.g., human plasma) or multiple aliquots of the same sample may be contacted separately with multiple types of particles 312 (e.g. each sample or aliquot may be contacted with one type of particle). Each particle may adsorb a unique subset of biomolecules from the samples 311 based in part on its physicochemical properties. Biomolecule coronas comprising the adsorbed biomolecules are separately analyzed 313 to generate particle-specific biomolecule corona data 314. The data may be expressed as arrays of intensities, for example as matrices of intensity values based on mass-to-charge ratios and elution times. The data may be collectively transformed into a common feature space (e.g. a hyperspectral data cube), with arrays of the biomolecule corona data corresponding to individual particle type, and dimensions of the arrays corresponding to sample ID and features of the biomolecule corona data.

A convolutional neural network 315 is applied to the biomolecule corona data. The convolutional neural network 315 contains a convolutional layer 316 composed of multiple kernels 317, each of which acts upon all sets of biomolecule corona data 314 to generate transformed data 318. Accordingly, the kernels perform combined analyses across all particle data (e.g., utilizing data from each particle to generate singular outputs. The convolutional layer 316 outputs the transformed data 318 to a neural network 319, which analyzes the transformed data to generate an output 320 such as a prediction of a biological state of the sample(s) 311.

(i) Machine Learning

Systems and methods of the present disclosure may utilize machine learning or a trained algorithm for data analysis. As used herein, "machine learning" can denote a computational process configured to utilize training data to optimize an algorithm for performing a task, while a trained classifier can refer to an algorithm generated with a machine learning framework. For example, a machine learning algorithm may utilize proteomic training data to generate a trained classifier to distinguish between samples of subjects with cancer and samples of healthy subjects such as subjects without cancer. A classifier may include a neural network. As machine learning algorithms may be unbound by input parameters, they may develop capabilities to identify complex patterns not discernible by humans. A system or method of the present disclosure may utilize unannotated data as training data for a machine learning algorithm or as input data for analysis by a trained classifier. Machine learning may be applied, and may include an averaged one-dependence estimator (AODE); a neural network, such as a convolutional neural network, backpropagation, an autoencoder, a Hopfield network, a Boltzmann machine, a restricted Boltzmann machine, a spiking neural network; Bayesian statistics, such as a Bayesian network or Bayesian knowledge base; case-based reasoning; Gaussian process regression; gene expression programming; group method of data handling (GMDH); inductive logic programming; instance-based learning; lazy learning; learning automata; learning vector quantization; a logistic model tree; minimum message length (e.g. a decision tree or a decision graph), such as a nearest neighbor algorithm or analogical modeling; probably approximately correct learning (PAC) learning; ripple down rules, a knowledge acquisition methodology; a symbolic machine learning algorithm; a support vector machine; a random Forest; an ensemble of classifiers, such as bootstrap aggregating (e.g. bagging) or boosting (e.g. a meta-algorithm); ordinal classification; an information fuzzy network (IFN); a conditional random field; analysis of variance (ANOVA); a linear classifier, such as Fisher's linear discriminant, linear regression, logistic regression, multinomial logistic regression, a naive Bayes classifier, a perceptron, a support vector machines; a quadratic classifier; k-nearest neighbor; boosting; decision trees, such as C4.5, random forests, ID3, CART, SLIQ SPRINT; a Bayesian network, such as Naive Bayes; or a hidden Markov model. Unsupervised learning may be applied, and may include an expectation-maximization algorithm; vector quantization; a generative topographic map; an information bottleneck method; an artificial neural network, such as a self-organizing map; association rule learning, such as, an Apriori algorithm, Eclat algorithm, or FPgrowth algorithm; hierarchical clustering, such as Singlelinkage clustering or conceptual clustering; cluster analysis, such as, a K-means algorithm, fuzzy clustering, DBSCAN, or an OPTICS algorithm; or outlier detection, such as local outlier factor. Semi-supervised learning may be applied, and may include a generative model; low-density separation; a graph-based method; or co-training. Reinforcement learning may be applied, and may include temporal difference learning; Q-learning; learning automata; or SARSA.

A computer-implemented system consistent with the present disclosure may comprise an artificial neural network. As used herein, "artificial neural network" may denote a machine learning algorithm configured to propagate data through multiple layers of processing units. Each processing unit may apply a function to input data before propagating the transformed data to a downstream processing unit. Artificial neural network processing units may be arranged in layers, such that data sequentially propagates through discrete layers of processing units. For example, an artificial neural network may comprise a first layer of processing units corresponding to input data structures, a second ("hidden") layer of processing units which receive and transform data from the first layer of processing units and pass the transformed data to a third layer of processing units which generate a single numerical output. Connections between processing units may comprise variable weights. For example, a first processing unit input may receive 0.2-times the output of a second processing unit and 0.8-times the output of a third processing unit. During training, connection weights and processing unit functions may be adjusted to optimize an aspect of an artificial neural network's performance. Two layers may contain different numbers of processing units.

An artificial neural network may comprise a convolutional layer, and in such cases may be referred to as a convolutional neural network. A convolutional layer may comprise a processing unit which filters input data. The filtering may reduce the dimensionality of the input dataset. For example, a convolutional neural network may accept a $10^4$ pixel by $10^4$ pixel image (e.g. an LC-MS spectrum) as an input, and in a first processing layer generate 100 separate $10^3$ by $10^3$ pixel images. Similarly, the convolutional neural network may accept an array or matrix of one size, and output another matrix or array of a different size. The filtering may also transform a dataset without modifying its dimensions. For example, the filtering may, without changing the size of an input GC-MS spectrum, sharpen peaks in a first window of the GC-MS spectrum and diminish peaks in a second window of the GC-MS spectrum. A processing unit may utilize a full input dataset (e.g., all $10^8$ pixels of an LC-MS spectrum), or a limited portion of an input dataset (e.g., 100 separate processing units within a processing layer each utilize separate $10^6$ pixel portions of a $10^8$ pixel input dataset).

Accordingly, an artificial neural network (e.g., a convolutional neural network) may condense complex input data (e.g., $10^9$ pixels worth of LC-MS spectral data) input relatively simple outputs (e.g., a vector with 3 elements corresponding to "healthy," "early-stage cancer," and "late-stage cancer"). By condensing large datasets, small and disparate features (e.g., unassignable peaks in the tail of a liquid-chromatogram) may be made to contribute to a biological state determination, thereby enhancing input data coverage relative to annotated data analysis.

In an aspect of the present disclosure, the system herein may comprise multiple modules. In some embodiments, a first module and a second module of the system may be configured to pre-process the raw data to be suitable for processing by the deep neural network for making prediction about a disease. In some cases, the first module may be configured to collect raw mass spectrometry data and convert it into a pseudo-image data. The raw spectrometry data may be tabular data at feature-level. The second module may be configured to transform the image data based on at least one of the mass spectrometry feature information. In some cases, a third module of the system is executed to train a deep neural network in a semi-supervised manner using contrastive learning. For example, the deep neural network may be trained to using data from human blood plasma samples originated from individuals diagnosed with a disease state or healthy individuals. The disease state may include a cancer such as pancreatic cancer.

Figure 3C:
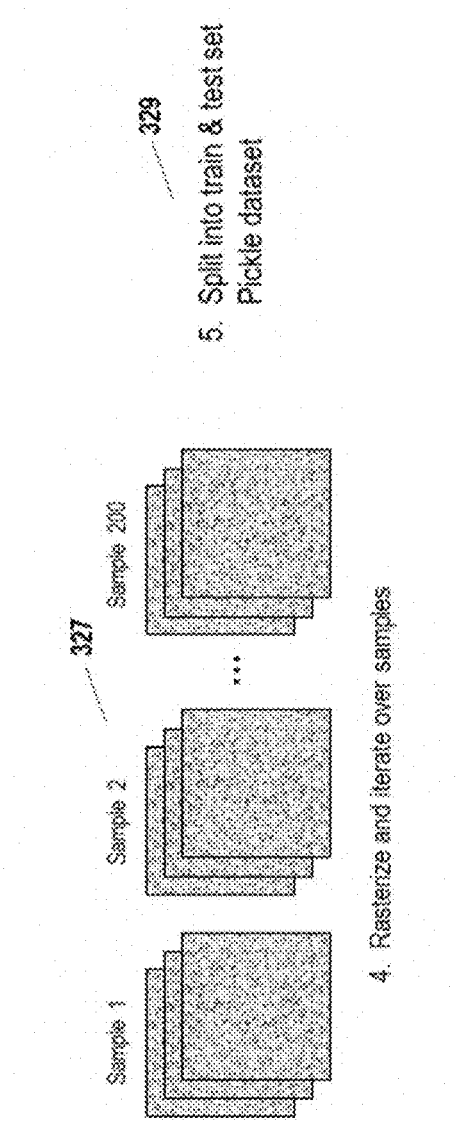
FIG. 3C shows examples of aspects that may be used in training a deep neural network.

FIG. 3C shows an exemplary method of training the deep neural network. In some embodiments of the training method, a first module may be employed to pre-process the raw mass spectrometry data. The pre-processing may comprise performing an alignment process and/or other image processing such as smoothing or denoise and the like as described elsewhere herein.

In some cases, the raw mass spectrometry data may be aligned according to one or more mass spectrometry features. FIG. 3C shows an example of the pre-processed mass spectrometry data aligned by features 321. As an example, a first module of the system may be configured to collect feature information of precursor ions (MS1) from a mass spectrometer. In some cases, a feature may comprise an ion's mass-charge ratio, charge, retention time, ion mobility and intensity. Unlike conventional mass spectrometry data processing where information is extracted based on known features (i.e., the meaning of peaks is known), the feature information herein may not assume knowing the feature information. For instance, the feature information utilized herein may include only the original information such as location of the peak intensity in the raw signal profile that is produced from the mass spectrometer. The feature information can be produced by any suitable feature finding algorithm (e.g., Bruker Feature Finder).

Figure 3D:
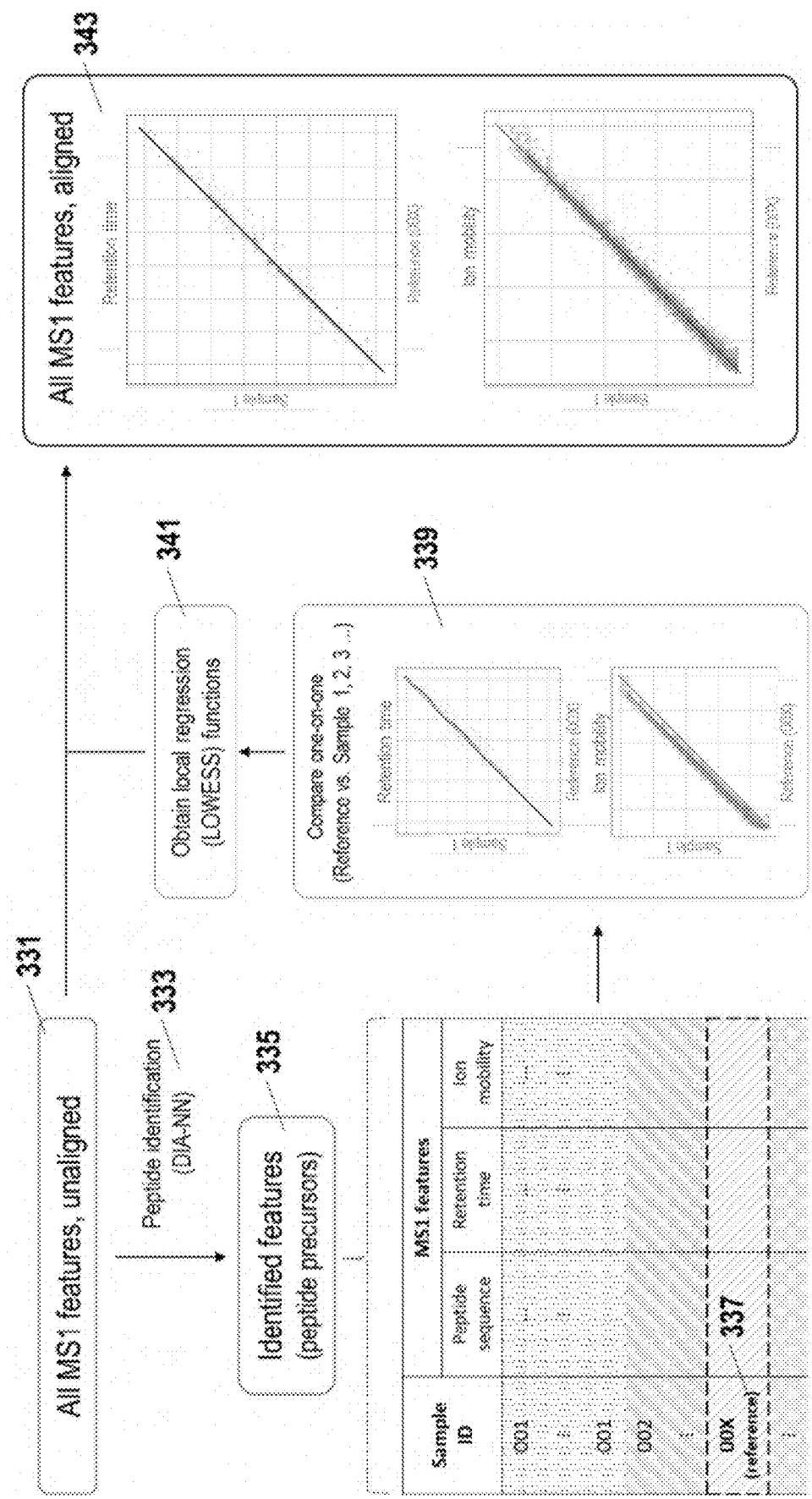
FIG. 3D shows examples of aspects that may be used in aligning data samples or mass spectrometry features.

Next, the data collected by the first module comprising a plurality of data samples may be aligned based on reference peptides. FIG. 3D shows an exemplary method of aligning data samples or mass spectrometry features. In some cases, the collected MS1 features may be unaligned 331 and processed to identify peptides based on the spectral library across all the samples. The peptide identification can be performed using any suitable methods or tools such as deep neural network for processing data independent acquisition (DIA) proteomics data (e.g., DIA-NN) 333. In some case, the peptides are identified for alignment purpose and only a portion of the all the peptides (e.g., identified features or peptide precursors 335) may need to be identified for the alignment purpose. For example, in some cases no more than 10%, 15%, 20%, 25%, 30%, 35%, 40%, 45%, 50% of the peptides may be identified to align all the samples. In some cases at least 1%, 2%, 3%, 4%, 5%, 10%, 15%, 20%, 25%, 30%, 35%, 40%, or 45%, of the peptides may be identified to align all the samples.

The first module may select a sample as reference 337 and align all the other sample runs to the selected sample. The reference sample may be selected based on any suitable criteria. For instance, a sample contains the highest number of identified peptides may be selected as a reference sample to which all the other sample runs may be aligned based on the identified peptides in each sample.

In some cases, to align each sample to the reference sample, each sample may be compared to the reference 339 and a local regression (e.g., LOWESS) may be performed 341 with the identified peptides that are present in both the reference sample and a given sample. The local regression function may also be referred to as a calibration function. In some cases the local regression function may be LOWESS (Locally Weighted Scatterplot Smoothing) or other non-parametric fitting. The alignment may be performed by finding a fitting curve for the peptides overlap between a given sample and the reference sample. For instance, at least ~1000 peptides typically overlap across the two samples and the fitting curve is generated on the retention times and ion mobility 339. Once the fitting curve is generated, the fitting curve function may be applied to all features of the given sample, including unidentified features. The alignment process is repeated to all the samples by comparing them to the reference sample until all the MS1 features are aligned 343. The output of the first module may comprise the aligned features.

As shown in FIG. 3C or FIG. 3D, the aligned features 321 may be stored in a tabular format comprising m/z, retention time, ion mobility and intensity in the columns. It should be noted that other suitable data structures may be utilized to store the aligned features.

Referring back to FIG. 3C, the second module of the system may convert the aligned features into pseudo images 327 that can be used to train the deep learning model 329. In some cases, the aligned MS1 features 321 may be loaded in the second module to create a plurality of two-dimensional (2D) images 327. For instance, one 2D image may be created for each sample by merging 3D image (e.g., three dimensions along m/z, retention time, ion mobility) over the ion mobility dimension 325. Each image 327 may be a two-dimensional array. In some cases, a 2D image may be downsized such as by utilizing rasterization. For instance, each element of the 2D array 327 may be calculated as a summation of log intensities of features collected in a bin (rasterization). In some cases, a bin may be along one or more dimensions (e.g., m/z, retention time). For instance, a bin may correspond to a specified range of m/z and retention time, and may not discriminate features based on ion mobilities. A bin size may be constant. For example, the full range across all features or samples may be equally split resulting in a number of splits in m/z (e.g., 200-3000 splits) and a number of splits in retention time (e.g., 200-600 splits). Alternatively, a bin size may be variable. In some cases, the bin does not discriminate features based on their different ion mobilities.

The number of splits in m/z may include at least 200 splits, at least 300 splits, at least 400 splits, at least 500 splits, at least 750 splits, at least 1000 splits, at least 1250 splits, at least 1500 splits, at least 1750 splits, at least 2000 splits, at least 2500 splits, or at least 2750 splits. The number of splits in m/z may include less than 250 splits, less than 300 splits, less than 400 splits, less than 500 splits, less than 750 splits, less than 1000 splits, less than 1250 splits, less than 1500 splits, less than 1750 splits, less than 2000 splits, less than 2500 splits, less than 2750 splits, or less than 3000 splits.

The number of splits in retention time may include at least 200 splits, at least 250 splits, at least 300 splits, at least 350 splits, at least 400 splits, at least 450 splits, at least 500 splits, or at least 550 splits. The number of splits in retention time may include less than 250 splits, less than 300 splits, less than 350 splits, less than 400 splits, less than 450 splits, less than 500 splits, less than 550 splits, or less than 600 splits.

(ii) Computer Systems

In addition to rasterizing the MS1 features and obtaining an image for each mass spectrometry run, the second module may also stack images to one another that originated from the same clinical sample. The aligned features from the same sample may be stacked and arranged into multiple channels each corresponding to a nanoparticle 323. As described above, MS runs originated from the same sample may have features show distinct peak patterns by adding different types of nanoparticle and their surface chemistry before each MS run. By assigning each image derived from one nanoparticle to a single-color channel, multiple channels MS runs or images may be combined in total, each corresponding to a channel (e.g., red, blue or green).

The images 327 may be split into training dataset and validation dataset for the deep neural network learning 329. The training dataset and the validation dataset may respectively include about 90% and about 10% of the total set, about 85% and about 15% of the total set, about 80% and about 20% of the total set, about 75% and about 25% of the total set, about 70% and about 30% of the total set, or any range between any of the aforementioned pairs of percentages. In some embodiments, a third module of the system may perform contrastive learning with a deep neural network utilizing the image data 327. For instance, the third module may load the dataset 327 and perform contrastive learning.

In some embodiments, the image dataset 327 may augmented prior to training the model. Data augmentation can yield accuracy benefits for contrastive learning. The data augmentation may comprise transforming an image by randomly changing the brightness, contrast, saturation and/or hue (so-called as Color Jitter1) such as with a probability 0.8, and by converting it to a grayscale with a probability 0.2. In some cases, the transformation may be repeated one or more times, thereby producing an augmented dataset. In some cases, the augmentation methods may comprise simulating various shift in the retention time dimension or ion mobility dimension. For example, the augmented images may be generated by shifting the original image along the retention time by certain pixels (e.g., corresponding to 5 seconds, 10 seconds, 20 seconds, 30 seconds, etc.), and/or along the ion mobility thereby creating variance across retention time range and/or mobility range. The augmented dataset may then be fed into a deep neural network for contrastive learning.

The contrastive learning may comprise two networks, a base encoder and a projection head. The neural network base encoder may extract representation vectors from the augmented data. The base encoder can have various network architecture. In some cases, the base encoder may be a pretrained ResNet-50 with parameters obtained from ImageNet. The projection head may be a small neural network that maps representations to the space where contrastive loss is applied. In some cases, the projection head herein is a fully connected layer (e.g., having its input dimension 1,000) and a binary output (e.g., an output dimension 2 for binary classification).

The base encoder and the projection head are trained to maximize agreement using a contrastive loss. A contrastive loss function is defined for a contrastive prediction task. The contrastive learning may advantageously reduce the requirement for labeled datasets where the training of the base encoder and the projection head may require only unlabeled dataset. For every epoch, a loss is computed using the augmented dataset without using sample labels. The neural network may be updated by mini batch gradient descent method. For example, the method may comprise randomly sampling a minibatch of N examples and defining the contrastive prediction task on pairs of augmented examples derived from the minibatch, resulting in 2N data points. Given a positive pair, the other 2(N−1) augmented examples are treated within a minibatch as negative examples.

After training is completed, the third module returns the base encoder and discards the projection head. The third module may then freeze the base encoder and optimize the fully connected layer using the labeled dataset. Once the network training is completed, an accuracy and a loss is computed using the validation dataset.

In some cases, the system may further comprise a model monitoring module for monitors data drift or performance of a model in different phases (e.g., development, deployment, prediction, validation, etc.). The model monitor system may also perform data integrity checks for models that have been deployed in a development, test, or production environment. The model monitor system may be configured to perform data/model integrity checks and detect data drift and accuracy degradation. The process may begin with detecting data drift in training data and prediction data. During training and prediction or detection, the model monitor system may monitor difference in distributions of training data, test, validation and prediction or detection data, change in distributions of training data, test, validation and prediction or detection data over time, covariates that are causing changes in the prediction output, and various others. The data monitored by the model monitor system may include data involved in model training and during production. The data at model training may comprise, for example, training, test and validation data, predictions, detections, or statistics that characterize the above datasets (e.g., mean, variance and higher order moments of the data sets). Data involved in production time may comprise time, input data, predictions made, and confidence bounds of predictions made. In some embodiments, the labels (e.g., ground truth data) may also be monitored. In some cases, the ground truth data may be monitored to evaluate the accuracy of a model and/or trigger retraining of the model. The model monitor system may monitor changes in data such as changes in ground truth data, or when new training data or prediction data becomes available. In some cases, continual training or improvement may be performed after deployment. In some cases, the deep neural network models may be improved or updated continuously over time (e.g., during implementation, after deployment). In some cases, the continual training and improvement may be performed automatically with little user input.

Figure 3E:
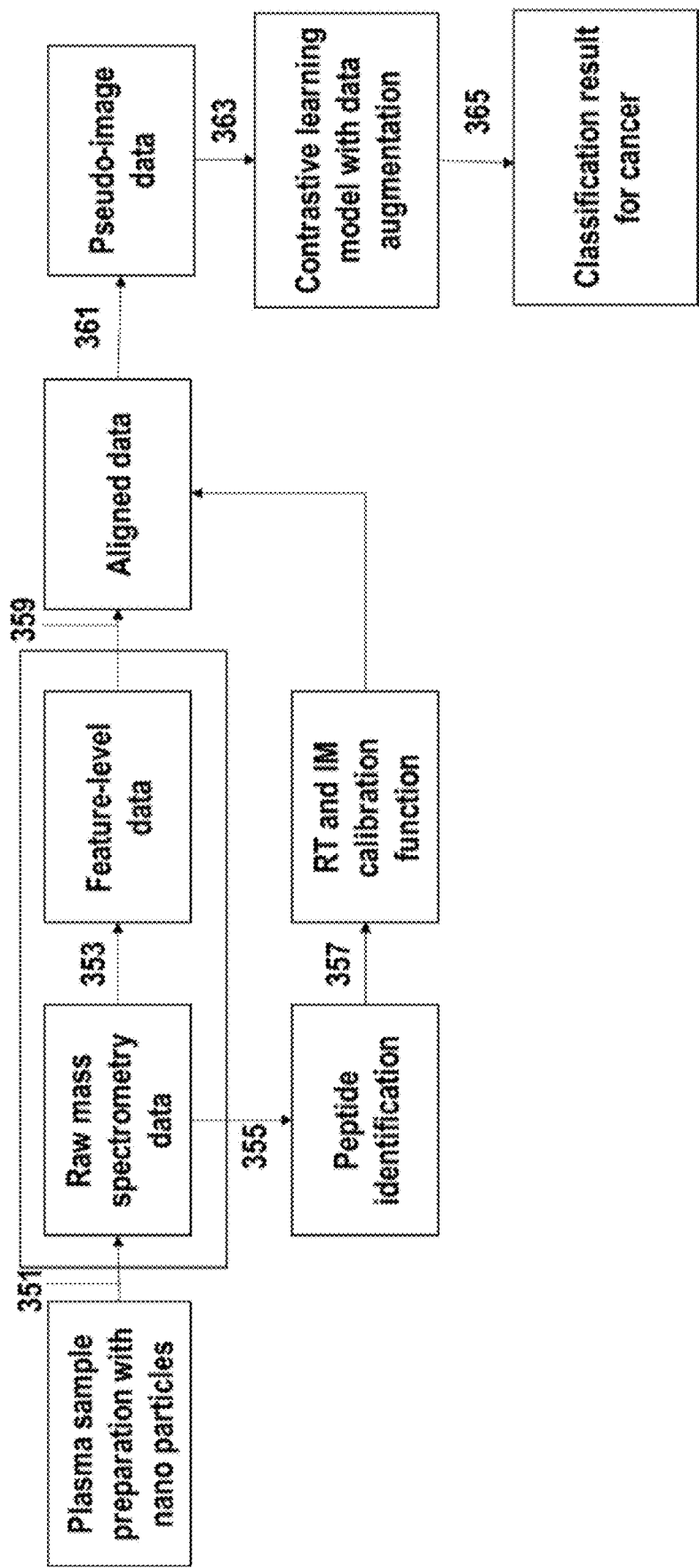
FIG. 3E is a flow chart showing some data processing aspects that may be used in the methods herein.

FIG. 3E shows an exemplary flow of data processing. As shown in the example, the raw data may be acquired by liquid chromatogram-based mass spectrometry supporting ion mobility. (e.g., Bruker TIMSTOF Pro) 351. The raw mass spectrometry data may then be processed by feature finding algorithm or software (e.g., Bruker 4D feature finder) to produce feature-level data 353. The feature level data may be stored in an output table, containing m/z, Retention Time (RT), ion mobility (IM), and intensity values or other data format depending on the software tool. The raw mass spectrometry data may also be processed to identify peptides 355 for feature alignment purpose as described elsewhere herein. For instance, peptides may be identified based on the spectrum matches by an identification algorithm and calibration functions for RT and IM may be calculated from identified precursor ions (i.e., peptides) 357. The calibration functions may be local regression (e.g., LOWESS) functions as described above. Next, the feature-level data or the raw data may be aligned for all the features based on the calibration functions 359. The aligned data may then be rasterized to form the pseudo-image data 361. The rasterization method can be the same as described above. For example, each element of the 2D array may be calculated as a summation of log intensities of features collected in a bin (rasterization) and the process may be iterated over the plurality of samples. The pseudo-image data may then be fed as input to the contrastive-based deep learning model with data augmentation 363. Once the classifier is trained, it may be deployed for inferring a result indicative of cancer or not 365.

Certain aspects of the methods described herein may be carried out using a computer system. For example, data analysis may be carried out using a computer system. Likewise, data may be obtained through the use of a computer system. A readout indicative of the presence, absence or amount of a biomolecule (e.g. protein, lipid, or metabolite) may be obtained at least in part using a computer system. The computer system may be used to carry out a method of using a classifier or neural network to assign a label corresponding to a presence, absence, or likelihood of a disease state to data, or to identify data as indicative or as not indicative of the disease state. The computer system may generate a report identifying a likelihood of the subject having a disease state. The computer system may transmit the report. For example, a laboratory may transmit a report regarding the disease state identification to a medical practitioner. A computer system may receive a report.

Figure 4:
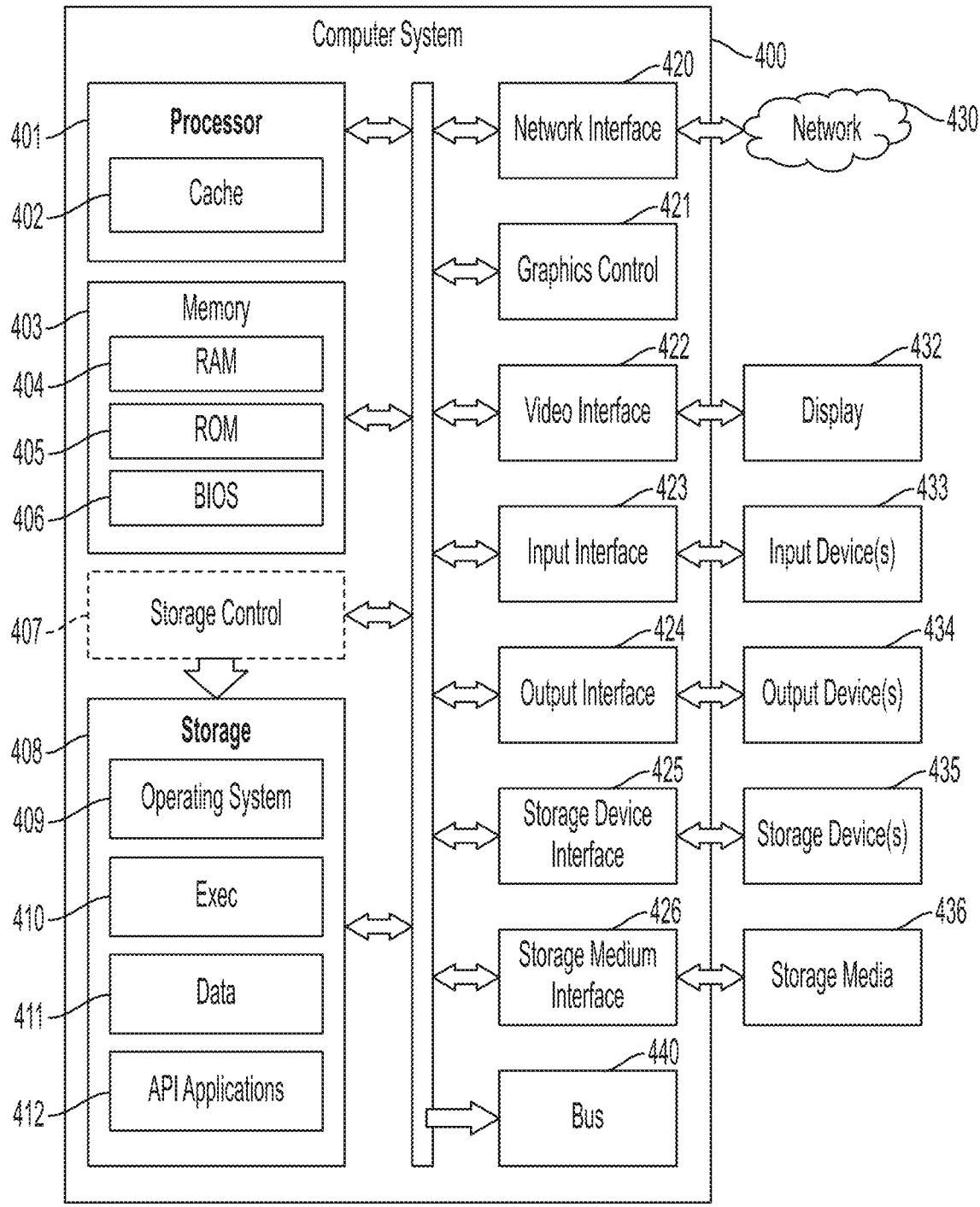
FIG. 4 shows a computer system that is programmed or otherwise configured to implement methods provided herein.

A computer system that carries out a method described herein may include some or all of the components shown in FIG. 4. Referring to FIG. 4, a block diagram is shown depicting an example of a machine that includes a computer system 400 (e.g., a processing or computing system) within which a set of instructions can execute for causing a device to perform or execute any one or more of the aspects and/or methodologies for static code scheduling of the present disclosure. The components in FIG. 4 are examples, and do not limit the scope of use or functionality of any hardware, software, embedded logic component, or a combination of two or more such components implementing particular aspects.

Computer system 400 may include one or more processors 401, a memory 403, and a storage 408 that communicate with each other, and with other components, via a bus 440. The bus 440 may also link a display 432, one or more input devices 433 (which may, for example, include a keypad, a keyboard, a mouse, a stylus, etc.), one or more output devices 434, one or more storage devices 435, and various tangible storage media 436. All of these elements may interface directly or via one or more interfaces or adaptors to the bus 440. For instance, the various tangible storage media 436 can interface with the bus 440 via storage medium interface 426. Computer system 400 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 400 includes one or more processor(s) 401 (e.g., central processing units (CPUs) or general purpose graphics processing units (GPGPUs)) that carry out functions. Processor(s) 401 optionally contains a cache memory unit 402 for temporary local storage of instructions, data, or computer addresses. Processor(s) 401 are configured to assist in execution of computer readable instructions. Computer system 400 may provide functionality for the components depicted in FIG. 4 as a result of the processor(s) 401 executing non-transitory, processor-executable instructions embodied in one or more tangible computer-readable storage media, such as memory 403, storage 408, storage devices 435, and/or storage medium 436. The computer-readable media may store software that implements particular aspects, and processor(s) 401 may execute the software. Memory 403 may read the software from one or more other computer-readable media (such as mass storage device(s) 435, 436) or from one or more other sources through a suitable interface, such as network interface 420. The software may cause processor(s) 401 to carry out one or more processes or one or more steps of one or more processes described or illustrated herein. Carrying out such processes or steps may include defining data structures stored in memory 403 and modifying the data structures as directed by the software.

The memory 403 may include various components (e.g., machine readable media) including, but not limited to, a random access memory component (e.g., RAM 404) (e.g., static RAM (SRAM), dynamic RAM (DRAM), ferroelectric random access memory (FRAM), phase-change random access memory (PRAM), etc.), a read-only memory component (e.g., ROM 405), and any combinations thereof. ROM 405 may act to communicate data and instructions unidirectionally to processor(s) 401, and RAM 404 may act to communicate data and instructions bidirectionally with processor(s) 401. ROM 405 and RAM 404 may include any suitable tangible computer-readable media described below. In one example, a basic input/output system 406 (BIOS), including basic routines that help to transfer information between elements within computer system 400, such as during start-up, may be stored in the memory 403.

Fixed storage 408 is connected bidirectionally to processor(s) 401, optionally through storage control unit 407. Fixed storage 408 provides additional data storage capacity and may also include any suitable tangible computer-readable media described herein. Storage 408 may be used to store operating system 409, executable(s) 410, data 411, applications 412 (application programs), and the like. Storage 408 can also include an optical disk drive, a solid-state memory device (e.g., flash-based systems), or a combination of any of the above. Information in storage 408 may, in appropriate cases, be incorporated as virtual memory in memory 403.

In one example, storage device(s) 435 may be removably interfaced with computer system 400 (e.g., via an external port connector (not shown)) via a storage device interface 425. Particularly, storage device(s) 435 and an associated machine-readable medium may provide non-volatile and/or volatile storage of machine-readable instructions, data structures, program modules, and/or other data for the computer system 400. In one example, software may reside, completely or partially, within a machine-readable medium on storage device(s) 435. In another example, software may reside, completely or partially, within processor(s) 401.

Bus 440 connects a wide variety of subsystems. Herein, reference to a bus may encompass one or more digital signal lines serving a common function, where appropriate. Bus 440 may be any of several types of bus structures including, but not limited to, a memory bus, a memory controller, a peripheral bus, a local bus, and any combinations thereof, using any of a variety of bus architectures. As an example and not by way of limitation, such architectures may include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, or any combination thereof.

Computer system 400 may also include an input device 433. In one example, a user of computer system 400 may enter commands and/or other information into computer system 400 via input device(s) 433. Examples of an input device(s) 433 include, but are not limited to, an alpha-numeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), or any combinations thereof. The input device may include a Kinect, Leap Motion, or the like. Input device(s) 433 may be interfaced to bus 440 via any of a variety of input interfaces 423 (e.g., input interface 423) including, but not limited to, serial, parallel, game port, USB, FIREWIRE, THUNDERBOLT, or any combination of the above.

When computer system 400 is connected to network 430, computer system 400 may communicate with other devices, specifically mobile devices and enterprise systems, distributed computing systems, cloud storage systems, cloud computing systems, and the like, connected to network 430. Communications to and from computer system 400 may be sent through network interface 420. For example, network interface 420 may receive incoming communications (such as requests or responses from other devices) in the form of one or more packets (such as Internet Protocol (IP) packets) from network 430, and computer system 400 may store the incoming communications in memory 403 for processing. Computer system 400 may similarly store outgoing communications (such as requests or responses to other devices) in the form of one or more packets in memory 403 and communicated to network 430 from network interface 420. Processor(s) 401 may access these communication packets stored in memory 403 for processing.

Examples of the network interface 420 include, but are not limited to, a network interface card, a modem, or any combination thereof. Examples of a network 430 or network segment 430 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, or any combinations thereof. A network, such as network 430, may employ a wired and/or a wireless mode of communication. In general, any network topology may be used.

Information and data can be displayed through a display 432. Examples of a display 432 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, or any combinations thereof. The display 432 can interface to the processor(s) 401, memory 403, and fixed storage 408, as well as other devices, such as input device(s) 433, via the bus 440. The display 432 is linked to the bus 440 via a video interface 422, and transport of data between the display 432 and the bus 440 can be controlled via the graphics control 421. The display may be a video projector. The display may be a head-mounted display (HMD) such as a VR headset. Suitable VR headsets may include HTC Vive, Oculus Rift, Samsung Gear VR, Microsoft HoloLens, Razer OSVR, FOVE VR, Zeiss VR One, Avegant Glyph, Freefly VR headset, or the like. The display may include a combination of devices such as those disclosed herein.

In addition to a display 432, computer system 400 may include one or more other peripheral output devices 434 including, but not limited to, an audio speaker, a printer, a storage device, or any combinations thereof. Such peripheral output devices may be connected to the bus 440 via an output interface 424. Examples of an output interface 424 include, but are not limited to, a serial port, a parallel connection, a USB port, a FIREWIRE port, a THUNDERBOLT port, or any combinations thereof.

In addition or as an alternative, computer system 400 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with aspects disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with aspects disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium. An example storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices may include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will also recognize that select televisions, video players, and digital music players with optional computer network connectivity are suitable for use in the system described herein. Suitable tablet computers may include those with booklet, slate, or convertible configurations.

The computing device may include an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. The operating system may be provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some cases, the platforms, systems, media, or methods disclosed herein include one or more non-transitory computer readable storage media encoded with a program including instructions executable by an operating system of a computer system. The computer system may be networked. A computer readable storage medium may be a tangible component of a computing device. A computer readable storage medium may be removable from a computing device. A computer readable storage medium may include any of, by way of non-limiting examples, CD-ROMs, DVDs, flash memory devices, solid state memory, magnetic disk drives, magnetic tape drives, optical disk drives, distributed computing systems including cloud computing systems and services, or the like. In some cases, the program and instructions are permanently, substantially permanently, semi-permanently, or non-transitorily encoded on the media.

c. Sample Types

Omic and multi-omic data may be generated from a sample of a subject. The sample may be a biofluid sample. Examples of biofluids include blood, serum, or plasma. Other examples of biofluids include urine, tears, semen, milk, vaginal fluid, mucus, saliva, or sweat. A biofluid may include a tissue or cell homogenate. A biofluid sample may be obtained from a subject. For example, a blood, serum, or plasma sample may be obtained from a subject by a blood draw. Other ways of obtaining biofluid samples include aspiration or swabbing. The biofluid sample may be cell-free or substantially cell-free. To obtain a cell-free or substantially cell-free biofluid sample, a biofluid may undergo a sample preparation method such as centrifugation and pellet removal.

A non-biofluid sample may be obtained from a subject. For example, a sample may include a tissue sample. The sample may be identified by a physician as at a high risk or low risk of being cancerous. The sample may include a cell sample. The sample may include a homogenate of a cell or tissue. The sample may include a supernatant of a centrifuged homogenate of a cell or tissue.

The sample can be obtained from the subject during any phase of a screening procedure, such as before, during, or after a tissue biopsy. The sample can be obtained before or during a stage where the subject is a candidate for a biopsy, for early detection of a disease. The sample can be obtained before or during a non-invasive work-up, an invasive work-up, treatment, a monitoring stage.

Data may be generated from a single sample, or from multiple samples. Data from multiple samples may be obtained from the same subject. In some cases, different data types are obtained from samples collected differently or in separate containers. A sample may be collected in a container that includes one or more reagents such as a preservation reagent or a biomolecule isolation reagent. Some examples of reagents include heparin, ethylenediaminetetraacetic acid (EDTA), citrate, an anti-lysis agent, or a combination of reagents. Samples from a subject may be collected in multiple containers that include different reagents, such as for preserving or isolating separate types of biomolecules. A sample may be collected in a container that does not include any reagent in the container. The samples may be collected at the same time (e.g. same hour or day), or at different times. A sample may be frozen, refrigerated, heated, or kept at room temperature.

Data or measurements described herein may relate to a number of samples. In some cases the methods described herein may be employed in a training set of less than 50, less than 100, less than 150, less than 200, less than 250, less than 300, less than 400, less than 500, less than 750, less than 1000, less than 1500, less than 2000, or less than 2500 samples. In some cases the methods described herein may be employed in a training set of at least 50, at least 100, at least 150, at least 200, at least 250, at least 300, at least 400, at least 500, at least 750, at least 1000, at least 1500, at least 2000, or at least 2500 samples. Some aspects relate to a classifier, or its use, where the classifier was trained or generated using any of the aforementioned numbers of samples.

A sample may include a non-biological sample. For example, any sample type that undergoes mass spectrometry may have the methods applied to the mass spectrometry data generated from the sample to distinguish between two (or more) sample types.

d. Data Generation

The methods disclosed herein may include obtaining data such as multi-omic data generated from one or more biofluid samples collected from a subject. The data may include biomolecule measurements such as protein measurements, lipid measurements, or metabolite measurements. The data may be annotated, partially annotated, or unannotated. The data may be or include an output from a mass spectrometry device. The data may relate to a presence, absence, or amount of a given biomolecule. The data may be labeled or identified as indicative of a disease or as not indicative of a disease.

Multiple biomolecule datasets may be generated from a single sample. In some cases, separate biomolecule data (e.g., protein data and lipid data) may be obtained by adjusting acquisition parameters on a single instrument. For example, separate biomolecule types may be detected from a single plasma sample across multiple LC-MS runs utilizing different mass ranges and liquid chromatography elution gradients. Alternatively or in combination, multiple biomolecule types may be separated from a single sample prior to analysis. As an example, a biofluid may be fractionated into peptides (e.g., through precipitation and pelleting), lipids (e.g., through extraction in a low polarity solvent, such as methyl tert-butyl ether), and metabolites (e.g., through extraction in aqueous:organic mixture, such as a water: methanol solution), which may each then be separately analyzed with LC-MS or GC-MS to generate separate omics datasets.

Some aspects refer to omic data. Omic data may comprise proteomic data, lipidomic data, metabolomic data, glycomics data, secretomics data, or any combination thereof. Omic data may include data on all biomolecules in a sample of a certain type such as proteins, transcripts, genetic material, or metabolites. Omic data may include data on a subset of the biomolecules. Omic data may include data on 500 or more, 750 or more, 1000 or more, 2500 or more, 5000 or more, 10,000 or more, 25,000 or more, biomolecules of a certain type.

(i) Protein Data

Biomolecule data may include protein data. Protein data may include data corresponding to proteins, peptides, peptoids, proteoforms, or any combination thereof. As used herein, the terms "peptide," "oligopeptide," "polypeptide," and "protein" may be used interchangeably to refer to at least two amino acids or amino acid analogs that are covalently linked by a peptide (amide) bond. For example, a protein may include one, two or more peptides bound together. A protein may also include any post-translational modifications. Proteomic data may include data about various proteoforms. Proteoforms can include different forms of a protein produced from a genome with any variety of sequence variations, splice isoforms, or post-translational modifications.

Protein data may include proteomic data. Proteomic data generally includes data on a number of proteins or peptides. For example, proteomic data may include information on the presence, absence, or amount of 1000 or more proteins or peptides. In some cases, proteomic data may include information on the presence, absence, or amount of 5000, 10,000, 20,000, or more peptides, proteins, or proteoforms. Proteomic data may even include up to about 1 million proteoforms. Proteomic data may include a range of proteins, peptides, or proteoforms defined by any of the aforementioned numbers of proteins, peptides, or proteoforms.

As with other biomolecules, protein data may be generated by a mass spectrometer or by mass spectrometry. An example of a mass spectrometry method includes use of high resolution, two-dimensional electrophoresis to separate proteins from different samples in parallel, followed by selection or staining of differentially expressed proteins to be identified by mass spectrometry. Another method uses stable isotope tags to differentially label proteins from two different complex mixtures. The proteins within a complex mixture may be labeled isotopically and then digested to yield labeled peptides. Then the labeled mixtures may be combined, and the peptides may be separated by multidimensional liquid chromatography and analyzed by tandem mass spectrometry. A mass spectrometry method may include use of liquid chromatography-mass spectrometry (LC-MS), a technique that may combine physical separation capabilities of liquid chromatography (e.g., HPLC) with mass spectrometry. Protein data may be generated from a sample after the sample has been treated to isolate or enrich proteins in the sample. Generating protein data may include concentrating, filtering, or centrifuging a sample.

In addition to any of the above methods, generating protein data may include contacting a sample with particles such that the particles adsorb biomolecules comprising proteins. The adsorbed proteins may be part of a biomolecule corona. The adsorbed proteins may be measured or identified in generating the protein data.

(ii) Lipid Data

Biomolecule data may include lipid data. Many organisms contain complex arrays of lipids (for example, humans express over 600 types of lipids), whose relative expression can serve as a powerful marker for biological state and health determinations. Lipids are a diverse class of biomolecules which include fatty acids (e.g., long carbohydrates with carboxylate tail groups), di-, tri-, and poly-glycerides, phospholipids, prenols, sterols (e.g., cholesterol), and ladderanes, among many other types. While lipids are primarily found in membranes, free, protein-complexed, and nucleic acid-complexed lipids are typically present in a range of biofluids, and in some cases may be differentially fractionated from membrane bound lipids. For example, lipid-binding proteins (e.g., albumin) may be collected from a sample by immunohistochemical precipitation, and then chemically induced to release bound lipids for subsequent collection and detection.

Lipid data may be generated from a sample after the sample has been treated to isolate or enrich lipids in the sample. Generating lipid data may include concentrating, filtering, or centrifuging a sample. Lipid analysis can comprise lipid fractionation. In many cases, lipids may be readily separated from other biomolecule types for lipid-specific analysis. As many lipids are strongly hydrophobic, organic solvent extractions and gradient chromatography methods can cleanly separate lipids from other biomolecule-types present within a sample. Lipid data may be generated using mass spectrometry. Lipid analysis may then distinguish lipids by class (e.g., distinguish sphingolipids from chlorolipids) or by individual type.

Lipid data may include lipidomic data. As with analysis of other biomolecules described herein, deep lipidomic profiling may be achieved without data annotation (e.g., lipid identifications), but instead with computer-implemented systems (e.g., convolutional neural network) analysis of raw lipidomic data. While subtle changes in lipid expression levels may not manifest in new, uniquely identifiable peaks, changes in lipid levels may generate discernible and consistent changes in lipidomic data, such as minor peak broadening, which may evidence particular biological states. LC-MS, GC-MS, NMR, HPLC, and gel electrophoresis, which are typically incapable of distinguishing individual lipids from complex mixtures, may thus be utilized for deep lipidomic interrogation.

(iii) Metabolite Data

Biomolecule data may include metabolite data. Metabolite data may include information on small-molecule (e.g., less than 1 kilodalton) metabolites (such as metabolic intermediates, hormones or other signaling molecules, or secondary metabolites). Metabolite data may involve data about metabolites. Metabolites may include substrates, intermediates or products of metabolism. A metabolite may be any molecule less than 1.5 kDa in size. Examples of metabolites may include sugars, lipids, amino acids, fatty acids, phenolic compounds, or alkaloids. Metabolite data may be distinguished by subtype, where each subtype includes a different type of metabolite.

Metabolite data may include information on the presence, absence, or amount of various metabolites. For example, metabolite data may include amounts of metabolites. A metabolite amount may be indicated as a concentration or quantity of metabolites, for example a concentration of a metabolite in a biofluid. A metabolite amount may be relative to another metabolite or to another biomolecule. Metabolite data may include information on the presence of metabolites. Metabolite data may include information on the absence of metabolites.

Metabolite data may include metabolomic data. Metabolomic data generally includes data on a number of metabolites. For example, metabolomic data may include information on the presence, absence, or amount of 1000 or more metabolites. In some cases, metabolomic data may include information on the presence, absence, or amount of 5000, 10,000, 20,000, 50,000, 100,000, 500,000, 1 million, 1.5 million, 2 million, or more metabolites, or a range of metabolites defined by any two of the aforementioned numbers of metabolites.

Lipid data may be generated from a sample after the sample has been treated to isolate or enrich lipids in the sample. Generating lipid data may include concentrating, filtering, or centrifuging a sample. Metabolite data may be generated by a mass spectrometer or by mass spectrometry. Mass spectrometry may include a separation method step such as liquid chromatography (e.g., HPLC). Mass spectrometry may include an ionization method such as electron ionization, atmospheric-pressure chemical ionization, electrospray ionization, or secondary electrospray ionization. Mass spectrometry may include surface-based mass spectrometry or secondary ion mass spectrometry. Another example of a method for generating metabolite data includes nuclear magnetic resonance (NMR). Other examples of methods for generating metabolite data include Fourier-transform ion cyclotron resonance, ion-mobility spectrometry, electrochemical detection (e.g. coupled to HPLC), or Raman spectroscopy and radiolabel (e.g. when combined with thin-layer chromatography). Some mass spectrometry methods described for generating metabolite data may be used for generating protein data or lipid data, or vice versa.

In addition to any of the above methods, generating metabolite data may include contacting a sample with particles such that the particles adsorb biomolecules comprising metabolites. The adsorbed metabolites may be part of a biomolecule corona. The adsorbed metabolites may be measured or identified in generating the metabolite data.

(iv) Use of Particles

A data generation method may comprise contacting a sample with a particle. The particle may adsorb a plurality of analytes (e.g., biomolecules such as proteins, lipids, or metabolites) from the sample, thereby generating a biomolecule corona comprising a subset of biomolecules from the sample. As biomolecule corona composition comprises dependencies on sample conditions (e.g., pH and osmolarity), biomolecule concentrations, and particle physicochemical properties, particle-based fractionation may provide a sensitive measure of sample composition.

Biomolecule corona formation can provide a handle for fractionating a sample. Following biomolecule corona formation on a particle, the particle may be separated from a sample by a range of methods, including filtration, magnetic immobilization (e.g., the particle is magnetically immobilized within a container as a sample is washed or removed), sedimentation, or any combination thereof. The biomolecule corona may then be separated from the particle (e.g., by sonication or further wash steps), or may be digested from the surface of the particle (e.g., biomolecule corona proteins may be proteolytically cleaved to generate solution-phase peptide fragments). The separated or digested biomolecules may then be analyzed to generate omic or multi-omic data.

In some cases, a plurality of particles may be used for biomolecule corona analysis or for sample fractionation. The plurality of particles may comprise a range of physicochemical properties lending to different thermodynamic favorabilities for biomolecule adsorption, and accordingly, the differing biomolecule corona compositions. Nonetheless, biomolecule coronas of distinct particle types will often share common biomolecules between their biomolecule coronas. For example, most particles, when contacted to human plasma, will adsorb at least a small quantity of human serum albumin. As the affinities of these common biomolecules for each particle depend not only on particle properties, but on sample composition, the relative abundances of biomolecules across different particle types can provide direct and indirect information regarding sample composition, and can thus be useful for classifying a biological state.

A plurality of particles may comprise particles with different physicochemical properties. The physicochemical properties may comprise composition, size, surface charge, hydrophobicity, hydrophilicity, surface functionality, surface topography, porosity, polarity, charge, surface curvature, shape, and any combination thereof. In some embodiments, the surface functionality comprises a small molecule functionalization Examples of biomolecules that may be adsorbed to particles include proteins, nucleic acids, lipids, saccharides, and metabolites. The adsorbed biomolecules may form a biomolecule corona on a surface of a particle. The adsorbed biomolecules may then optionally be further fractionated (e.g., by biomolecule type), and measured or identified by a variety of analytical methods.

Particles can be made from various materials. Such materials may include metals, magnetic particles, polymers, or lipids. A particle may be made from a combination of materials. A particle may comprise layers of different materials. The different materials may have different properties. A particle may include a core comprised of a first material and a shell comprised of a second material. The core and the shell may have different properties. The core or the shell may be magnetic, thereby enabling magnetic particle immobilization for washing and separation steps.

A particle may comprise a metal or a metal oxide. For example, a particle may include gold, silver, copper, nickel, cobalt, palladium, platinum, iridium, osmium, rhodium, ruthenium, rhenium, vanadium, chromium, manganese, niobium, molybdenum, tungsten, tantalum, iron, or cadmium, or a combination thereof.

A particle may be magnetic (e.g., ferromagnetic or ferrimagnetic). A particle comprising iron oxide may be magnetic. A particle may include a superparamagnetic iron oxide nanoparticle (SPION).

A particle may include a polymer. Examples of polymers include polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, a polyalkylene glycol (e.g., polyethylene glycol (PEG)), a polyester (e.g., poly(lactide-co-glycolide) (PLGA), polylactic acid, or polycaprolactone), or a copolymer of two or more polymers, such as a copolymer of a polyalkylene glycol (e.g., PEG) and a polyester (e.g., PLGA). A particle may be made from a combination of polymers.

A particle may include a lipid. Examples of lipids include dioleoylphosphatidylglycerol (DOPG), diacylphosphatidylcholine, diacylphosphatidylethanolamine, ceramide, sphingomyelin, cephalin, cholesterol, cerebrosides and diacylglycerols, dioleoylphosphatidylcholine (DOPC), dimyristoylphosphatidylcholine (DMPC), and dioleoylphosphatidylserine (DOPS), phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, or cholesterol. A particle may be made from a combination of lipids.

Further examples of materials include silica, carbon, carboxylate, polyacrylic acid, carbohydrates, dextran, polystyrene, dimethylamine, amines, or silanes. Some examples of particles include a carboxylate SPION, a phenol-formaldehyde coated SPION, a silica-coated SPION, a polystyrene coated SPION, a carboxylated Poly(styrene-co-methacrylic acid), P(St-co-MAA) coated SPION, a N-(3-Trimethoxysilylpropyl)diethylenetriamine coated SPION, a poly(N-(3-(dimethylamino)propyl) methacrylamide) (PDMAPMA)-coated SPION, a 1,2,4,5-Benzenetetracarboxylic acid coated SPION, a poly(vinylbenzyltrimethylammonium chloride) (PVBTMAC) coated SPION, carboxylate coated with peracetic acid, a poly(oligo(ethylene glycol) methyl ether methacrylate) (POEGMA)-coated SPION, a polystyrene carboxyl functionalized particle, a carboxylic acid particle, a particle with an amino surface, a silica amino functionalized particle, a particle with a Jeffamine surface, or a silica silanol coated particle.

Particles of various sizes may be used. The particles may include nanoparticles. Nanoparticles may be from about 10 nm to about 1000 nm in diameter. For example, the nanoparticles can be at least 10 nm, at least 100 nm, at least 200 nm, at least 300 nm, at least 400 nm, at least 500 nm, at least 600 nm, at least 700 nm, at least 800 nm, at least 900 nm, from 10 nm to 50 nm, from 50 nm to 100 nm, from 100 nm to 150 nm, from 150 nm to 200 nm, from 200 nm to 250 nm, from 250 nm to 300 nm, from 300 nm to 350 nm, from 350 nm to 400 nm, from 400 nm to 450 nm, from 450 nm to 500 nm, from 500 nm to 550 nm, from 550 nm to 600 nm, from 600 nm to 650 nm, from 650 nm to 700 nm, from 700 nm to 750 nm, from 750 nm to 800 nm, from 800 nm to 850 nm, from 850 nm to 900 nm, from 100 nm to 300 nm, from 150 nm to 350 nm, from 200 nm to 400 nm, from 250 nm to 450 nm, from 300 nm to 500 nm, from 350 nm to 550 nm, from 400 nm to 600 nm, from 450 nm to 650 nm, from 500 nm to 700 nm, from 550 nm to 750 nm, from 600 nm to 800 nm, from 650 nm to 850 nm, from 700 nm to 900 nm, or from 10 nm to 900 nm in diameter. A nanoparticle may be less than 1000 nm in diameter. Some examples include diameters of about 50 nm, about 130 nm, about 150 nm, 400-600 nm, or 100-390 nm.

The particles may include microparticles. A microparticle may be a particle that is from about 1 μm to about 1000 μm in diameter. For example, the microparticles can be at least 1 μm, at least 10 μm, at least 100 μm, at least 200 μm, at least 300 μm, at least 400 μm, at least 500 μm, at least 600 μm, at least 700 μm, at least 800 μm, at least 900 μm, from 10 μm to 50 μm, from 50 μm to 100 μm, from 100 μm to 150 μm, from 150 μm to 200 μm, from 200 μm to 250 μm, from 250 μm to 300 μm, from 300 μm to 350 μm, from 350 μm to 400 μm, from 400 μm to 450 μm, from 450 μm to 500 μm, from 500 μm to 550 μm, from 550 μm to 600 μm, from 600 μm to 650 μm, from 650 μm to 700 μm, from 700 μm to 750 μm, from 750 μm to 800 μm, from 800 μm to 850 μm, from 850 μm to 900 μm, from 100 μm to 300 μm, from 150 μm to 350 μm, from 200 μm to 400 μm, from 250 μm to 450 μm, from 300 μm to 500 μm, from 350 μm to 550 μm, from 400 μm to 600 μm, from 450 μm to 650 μm, from 500 μm to 700 μm, from 550 μm to 750 μm, from 600 μm to 800 μm, from 650 μm to 850 μm, from 700 μm to 900 μm, or from 10 μm to 900 μm in diameter. A microparticle may be less than 1000 μm in diameter. Some examples include diameters of 2.0-2.9 μm.

The particles may include physiochemically distinct sets of particles (for example, 2 or more sets of physiochemically particles where 1 set of particles is physiochemically distinct from another set of particles. Examples of physiochemical properties include charge (e.g., positive, negative, or neutral) or hydrophobicity (e.g. hydrophobic or hydrophilic). The particles may include 2, 3, 4, 5, 6, 7, 8, 9, 10, 11, 12, 13, 14, 15, 16, 17, 18, 19, 20, or more sets of particles, or a range of sets of particles including any of the numbers of sets of particles.

e. Subjects and Treatment

The methods described herein may be used to identify a subject as likely to have a disease state or not. The subject may be an organism. The subject may be an animal. The subject may be a vertebrate. The subject may be a mammal. The subject may be a human. The subject may be male or female. In some cases, the subject may be a plant, fungus, or other animal. The subject may be a microorganism. The microorganism may be a bacteria. The microorganism may include a virus. The subject may have a disease state. For example, the subject may have a disease or disorder may be healthy.

A sample may be obtained from the subject for purposes of identifying a disease state in the subject. The subject may be suspected of having the disease state or as not having the disease state. The method may be used to confirm or refute the suspected disease state.

In some cases, the subject is monitored. For example, information about a likelihood of the subject having a disease state may be used to determine to monitor a subject without providing a treatment to the subject. In other circumstances, the subject may be monitored while receiving treatment to see if a disease state in the subject improves.

When the subject is identified as not having the disease state, the subject may avoid an otherwise unfavorable disease treatment (and associated side effects of the disease treatment), or is able to avoid having to be biopsied or tested invasively for the disease state. When the subject is identified as not having the disease state, the subject may be monitored without receiving a treatment. When the subject is identified as not having the disease state, the subject may be monitored without receiving a biopsy. In some cases, the subject identified as not having the disease state may be treated with palliative care such as a pharmaceutical composition for pain. In some cases, the subject is identified as having another disease different from the initially suspected disease state, and is provided treatment for the other disease.

When the subject is identified as having the disease state, the subject may be provided a treatment for the disease state. For example, if the disease state is cancer, the subject may be provided a cancer treatment. Examples of treatments include surgery, organ transplantation, administration of a pharmaceutical composition, radiation therapy, chemotherapy, immunotherapy, hormone therapy, monoclonal antibody treatment, stem cell transplantation, gene therapy, or chimeric antigen receptor (CAR)-T cell or transgenic T cell administration.

When the subject is identified as having the disease state, the subject may be further evaluated for the disease state. For example, a subject suspected of having the disease state may be subjected to a biopsy after a method disclosed herein indicates that he or she may have the disease state.

Some cases include recommending a treatment or monitoring of the subject. For example, a medical practitioner may receive a report generated by a method described herein. The report may indicate a likelihood of the subject having a disease state. The medical practitioner may then provide or recommend the treatment or monitoring to the subject or to another medical practitioner. Some cases include recommending a treatment for the subject. Some cases include recommending monitoring of the subject f. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

As used herein, the term "about" a number refers to that number plus or minus 15% of that number. The term "about" a range refers to that range minus 15% of its lowest value and plus 15% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The section headings used herein are for organizational purposes only and are not to be construed as limiting the subject matter described.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

EXAMPLES

Example 1. Direct Classification of Raw Mass Spectrometry Data

Raw mass spectrometry data obtained from biofluid samples of patients with and without cancer were directly classified using methods described herein.

Figure 3F:
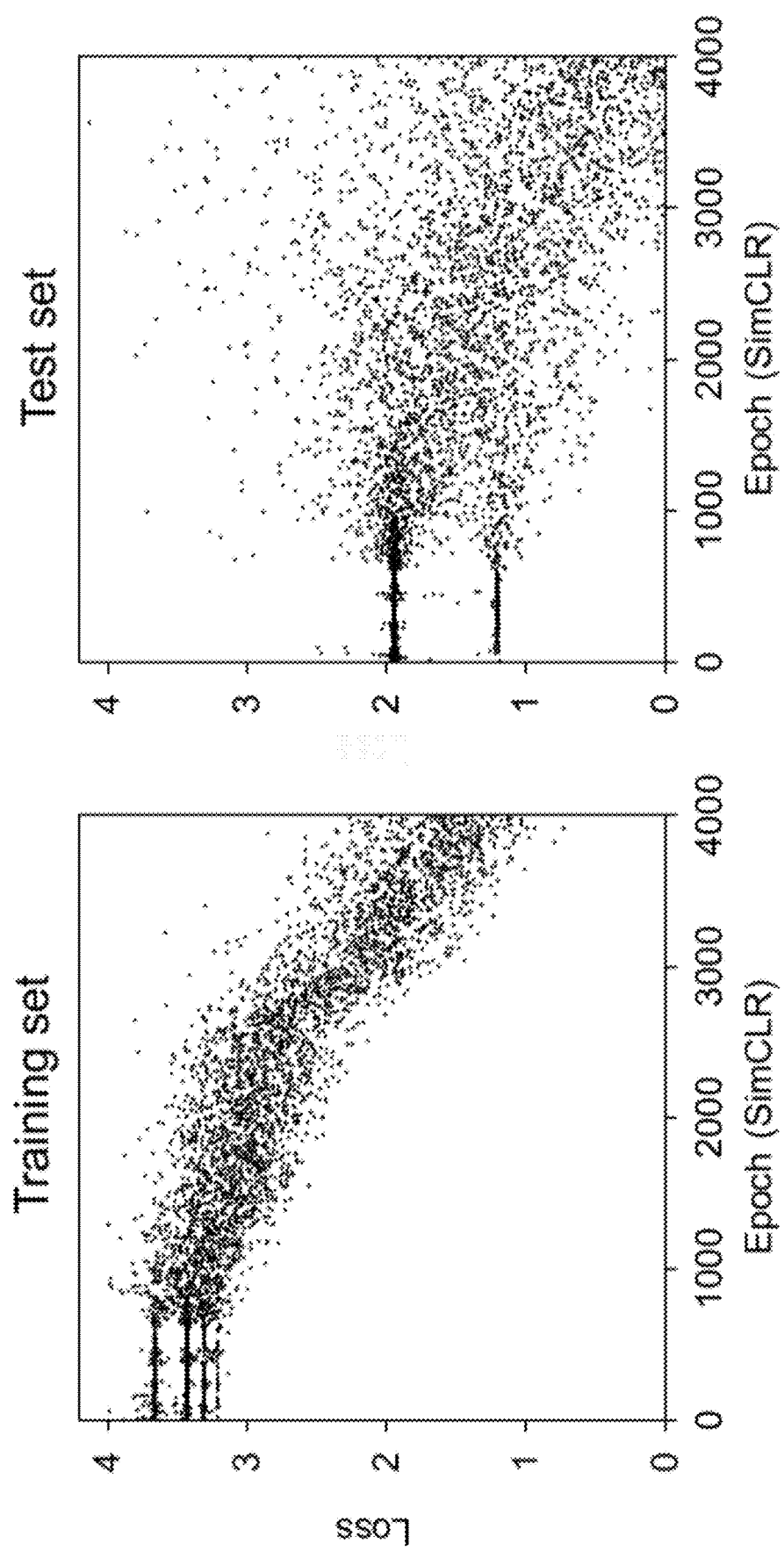
FIG. 3F shows results of a classifier using methods described herein.
Figure 3G:
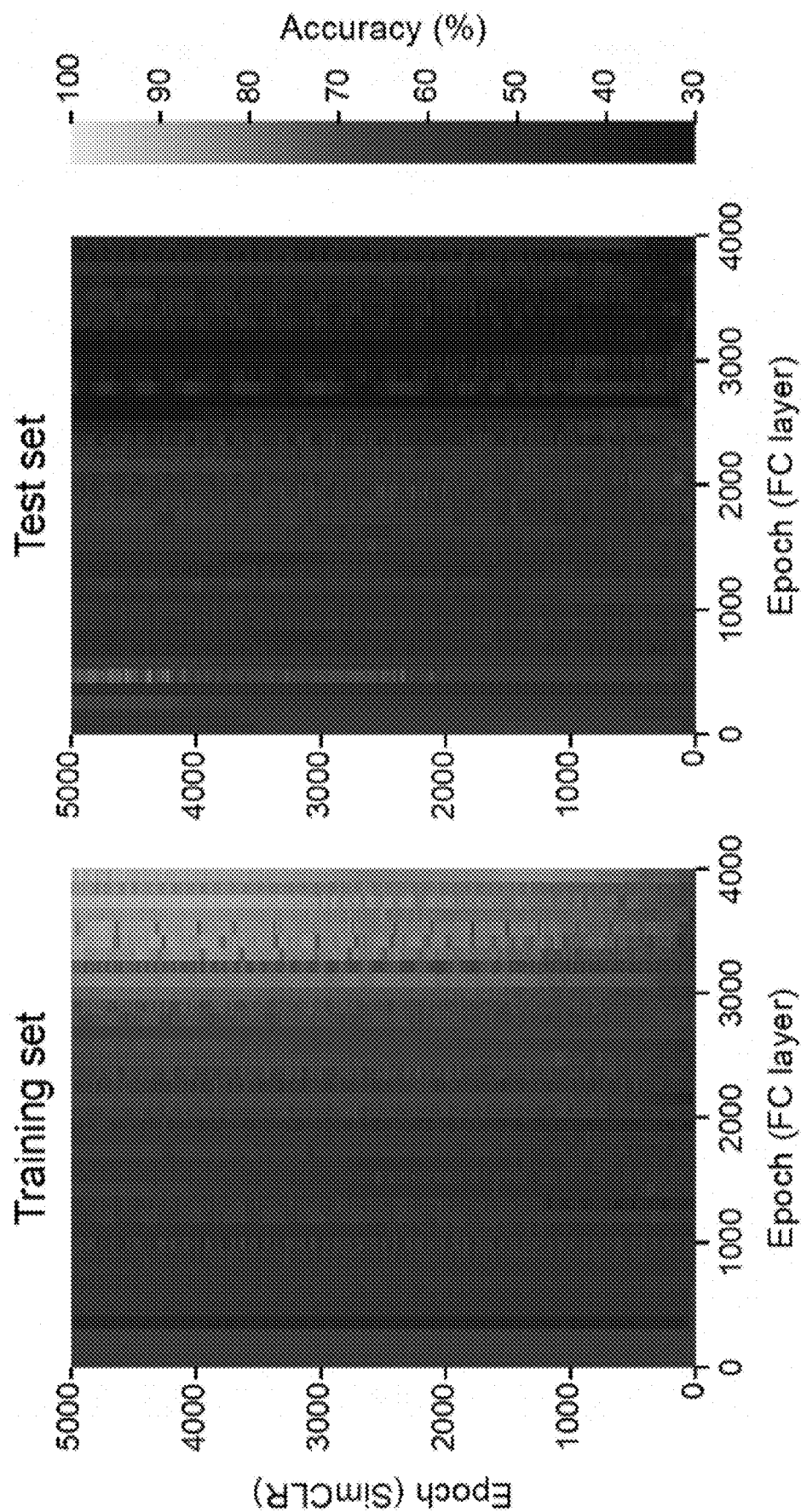
FIG. 3G shows results of a classifier using methods described herein.

FIG. 3F and FIG. 3G shows results of a classifier trained and applied using the methods described herein, particularly the methods in FIG. 3C-3E. In the example, the classifier was trained using contrastive learning with data augmentation. The data was obtained from 196 biofluid samples that included plasma from 92 human subjects with cancer, and plasma from 104 control human subjects without cancer. The cancer was pancreatic cancer. The data was split into a training data set (80%) and test/validation data set (20%). FIG. 3F shows a loss curve of the model measured on training set and test set over epochs with a learning algorithm described above. FIG. 3G shows the heatmap plot of model accuracy measured on training set (left) and test set (right). The model was trained by a given number of epochs with the provided deep neural network (y axis) and the fully connected layer (x axis). Overall, the classifier could successfully distinguish between the healthy samples and samples of subjects having cancer.

The results indicate that the methods described herein are useful for distinguishing a subject characteristic when the classifier is trained using two separate populations. In addition to cancer, the methods described herein may be used to classify other disease states, a healthy state, or any other aspect. The methods may be applied to human samples as well as non-human or non-biological samples to distinguish or identify aspects of the samples.

Wet Lab Steps for Example 1

Plasma samples were processed through the Proteograph (Seer, Redwood City, CA) using a five nanoparticle panel and process controls following the manufacturer's protocol. Eluted peptide concentration was measured using a quantitative fluorometric peptide assay kit (Thermo Fisher, Waltham, MA) and dried down in a Centrivap vacuum concentrator (LabConco, Kansas City, MO) at room temperature overnight. Dried peptides were sealed and stored at −80° C. until reconstitution. Prior to reconstitution, peptides were equilibrated at room temperature for 30 min and then reconstituted on the Proteograph in 0.1% formic acid (Thermo Fisher, Waltham, MA) in LCMS-grade water (Honeywell, Charlotte, NC,) spiked with heavy-labeled retention time peptide standards—iRT (Biogynosys, Switzerland) and Pepcal (SciEX, Redwood City, CA) prepared according to manufacturer's instructions. Peptides from Nanoparticles 1-4 were reconstituted to 30 ng/μL while Nanoparticle 5 peptides were reconstituted to 15 ng/μL. Reconstituted peptides were homogenized in solution by shaking for 10 min @ 1000 rpm at room temperature on an orbital shaker (Bioshake, Germany) and spun down briefly (~10 secs) in a centrifuge (Eppendorf, Germany).

Reconstituted peptides were loaded onto Evotips (Evosep, Denmark) packed with C18 resin following the manufacturer's protocol. LCMS-grade water and acetonitrile were purchased from Honeywell (Charlotte, NC), formic acid was purchased from Thermo Fisher (Waltham, MA) and 2-propanol was purchased from EMD Millipore (Burlington, MA). 0.1% Formic acid in water (Solvent A) and 0.1% formic acid in acetonitrile (Solvent B) were prepared for both the preparation of Evotips and for the Evosep One LC system. After each step, tips were centrifuged for 1 min @ 700 g (Eppendorf, Germany). Evotips were first washed with Solvent B, conditioned with 2-propanol for 15 secs and then washed with Solvent A. Evotips were placed in Solvent A while reconstituted peptides were loaded on the Evotips. Evotips now loaded with sample were washed with Solvent A. 200 μL of Solvent A were added to Evotips in addition to placing them in Solvent A to keep the C18 resin wet during LCMS analysis.

Evotips were placed on the Evosep One LC system (Evosep, Denmark) and peptides were separated on a reversed-phase 8 cm×150 μM, 1.5 μM, 100 Å column packed with C18 resin (Pepsep, Denmark) using a 60 samples per day (21 min gradient) Evosep LC method. 600 ng of Nanoparticle 1-4 and 300 ng of Nanoparticle 5 were loaded on the Evotips.

Peptides fractionated on the Evosep system were analyzed on a timsTOF Pro II (Bruker, Germany) using Data Independent Acquisition mode with Parallel accumulation-serial fragmentation (DIA-PASEF) using the following parameters: Source capillary voltage was set to 1700 V and 200° C. Precursors (MS1) across m/z 100-1700 and within an ion mobility window spanning $1/K0$ 0.84-1.31 V·s/cm2 were fragmented using collision energies following a linear step-function ranging between 20 eV-63 eV. Tims cell accumulation time was set at 100 ms and the ramp time at 85 ms. Resulting MS/MS fragment spectra between m/z 390-1250 were analyzed using a DIA schema with 57 Da windows (15 mass steps) with no mass/mobility overlap resulting in a cycle time of just under 0.8 s.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system comprising:
   a communication interface that is configured to receive data over a communication network, the data comprising arrays of intensity values based on mass-to-charge ratios, retention time, ion mobility, or elution times, wherein each array of intensity values of the arrays of intensity values correspond to distinct groups of biological species of one or more biological samples; and
   a computer system in communication with the communication interface, wherein the computer system comprises one or more computer processors and a computer readable medium comprising machine-executable code that, upon execution by the one or more computer processors, implements a method comprising:
   (a) combining the arrays of intensity values to generate a multi-dimensional image dataset by at least aligning the arrays of intensity values based on identified mass spectrometry features; and
   (b) applying a classifier to the multi-dimensional image dataset to generate a label corresponding to a biological state, wherein the classifier is trained using an augmented training dataset comprising shifting an image along the mass-to-charge ratios, the retention time, the ion mobility, or the elution times.

2. The system of claim 1, wherein the classifier is trained using contrastive learning.

3. The system of claim 2, wherein the contrastive learning comprises the augmented training dataset.

4. The system of claim 1, wherein the multi-dimensional image dataset comprises a higher dimensionality than any one of the arrays of intensity values.

5. The system of claim 1, wherein the multi-dimensional image dataset comprises a hyperspectral data cube.

6. The system of claim 1, wherein the multi-dimensional image dataset comprises another image, or wherein the arrays of intensity values comprise images.

7. The system of claim 1, wherein the classifier comprises features corresponding to the mass-to-charge ratios and the elution times.

8. The system of claim 7, wherein the classifier generates the label based on a subset of the features.

9. The system of claim 7, wherein the features are identified from training datasets obtained from subjects having the biological state and from subjects not having the biological state.

10. The system of claim 9, wherein the features are identified from the training datasets by scanning the training datasets for differences in raw mass spectrometry data.

11. The system of claim 1, wherein the intensity values in the array of intensity values relate to abundances of the distinct groups of biological species.

12. The system of claim 1, wherein the intensity values in the array of intensity values are generated by mass spectrometry.

13. The system of claim 1, wherein the distinct groups of biological species are ionized by a method comprising a chemical ionization, plasma and glow discharge, electron impact, electrospray ionization, fast-atom bombardment, field ionization, laser ionization, matrix-assisted laser desorption ionization, plasma-desorption ionization, resonance ionization, secondary ionization, spark source, or thermal ionization.

14. The system of claim 1, wherein the distinct groups of biological species comprise proteins or peptides.

15. The system of claim 1, wherein the distinct groups of biological species have been adsorbed to nanoparticles.

16. The system of claim 1, wherein the one or more biological samples comprise a biofluid sample.

17. The system of claim 1, wherein the biological state comprises a healthy state or a disease state.

18. The system of claim 17, wherein the disease state is a cancer state.

19. The system of claim 1, wherein the method further comprises augmenting the image of the multi-dimensional image dataset, wherein the augmenting comprises shifting the image along the mass-to-charge ratios, the retention time, the ion mobility, or the elution times.

20. The system of claim 1, wherein the method further comprises training the classifier with the augmented training dataset.

* * * * *